(12) United States Patent
Nagai et al.

(10) Patent No.: US 7,897,821 B2
(45) Date of Patent: Mar. 1, 2011

(54) SULFONIUM COMPOUND

(75) Inventors: Tomoki Nagai, Tokyo (JP); Eiji Yoneda, Tokyo (JP); Takuma Ebata, Tokyo (JP); Takanori Kawakami, Tokyo (JP); Makoto Sugiura, Tokyo (JP); Tsutomu Shimokawa, Tokyo (JP); Makoto Shimizu, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 12/873,265

(22) Filed: Aug. 31, 2010

(65) Prior Publication Data

US 2010/0324329 A1 Dec. 23, 2010

Related U.S. Application Data

(63) Continuation of application No. 11/914,024, filed as application No. PCT/JP2006/309446 on May 11, 2006.

(30) Foreign Application Priority Data

| May 11, 2005 | (JP) | 2005-138351 |
| May 23, 2005 | (JP) | 2005-150156 |
| Feb. 3, 2006 | (JP) | 2006-027388 |

(51) Int. Cl.
   *C07C 31/34* (2006.01)
(52) U.S. Cl. .................. 568/842; 568/28
(58) Field of Classification Search ............ 568/28, 568/842
   See application file for complete search history.

(56) References Cited

U.S. PATENT DOCUMENTS

| 3,984,495 A | 10/1976 | Okamura et al. |
| 4,421,889 A | 12/1983 | Braun et al. |
| 5,414,117 A | 5/1995 | Armand et al. |
| 5,548,055 A | 8/1996 | Narang et al. |

(Continued)

FOREIGN PATENT DOCUMENTS

DE    25 35 372    8/1975

(Continued)

OTHER PUBLICATIONS

European Search Report issued by the European Patent Office.

(Continued)

*Primary Examiner*—David Wu
*Assistant Examiner*—Vu A Nguyen
(74) *Attorney, Agent, or Firm*—Ditthavong Mori & Steiner, P.C.

(57) ABSTRACT

A compound is shown by the following formula (5) in which at least one of $R_f$ groups represents a fluorine atom or a linear or branched perfluoroalkyl group having 1 to 10 carbon atoms, A' represents a substituted or unsubstituted, linear or branched alkylene group having 1 to 20 carbon atoms, an alkylene group having at least one hetero atom, or a single bond, G represents a divalent organic group having a fluorine atom or a single bond, $M^{m+}$ represents an onium cation, m represents a natural number of 1 to 3, and p represents a natural number of 1 to 8.

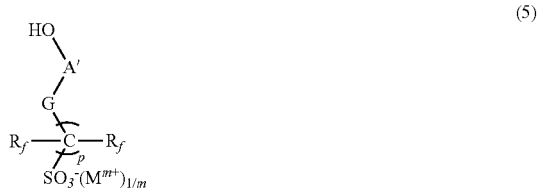

(5)

1 Claim, 2 Drawing Sheets

U.S. PATENT DOCUMENTS

| | | | |
|---|---|---|---|
| 5,627,292 | A | 5/1997 | Armand et al. |
| 5,945,250 | A | 8/1999 | Aoai et al. |
| 5,998,559 | A | 12/1999 | Narang et al. |
| 2004/0072094 | A1 | 4/2004 | Shima et al. |
| 2006/0228648 | A1 | 10/2006 | Ohsawa et al. |

FOREIGN PATENT DOCUMENTS

| | | |
|---|---|---|
| DE | 44 31 053 | 1/1994 |
| EP | 0 699 726 | 12/1995 |
| JP | 48-27906 | 8/1973 |
| JP | 05-188598 | 7/1993 |
| JP | 6-12452 | 2/1994 |
| JP | 6-509811 | 11/1994 |
| JP | 08-325475 | 12/1996 |
| JP | 09-325497 | 12/1997 |
| JP | 10-221852 | 8/1998 |
| JP | 11-502543 | 3/1999 |
| JP | 2002-145955 | 5/2002 |
| JP | 2002-201232 | 7/2002 |
| JP | 2003-173026 | 6/2003 |
| JP | 2003-525957 | 9/2003 |
| JP | 2004-62154 | 2/2004 |
| WO | WO 93/16988 | 9/1993 |
| WO | WO 96/21953 | 7/1996 |
| WO | WO 99/67304 | 12/1999 |

OTHER PUBLICATIONS

J.M.G. Cowie, et al., "Novel single ion, comb-branched polymer electrolytes," Solid State Ionics, 1999, 123 (1-4), pp. 233-242 (Experimental section).

SULFONIUM COMPOUND

CROSS-REFERENCE TO RELATED APPLICATIONS

This application is a continuation application of U.S. patent application Ser. No. 11/914,024 filed Feb. 28, 2008, which in turn is the U.S. National Stage Application of International Application No. PCT/JP2006/309446 filed May 11, 2006, which in turn claims priority to Japanese Patent Application No. 2005-138351 filed May 11, 2005, Japanese Patent Application No. 2005-150156 filed May 23, 2005, and Japanese Patent Application No. 2006-027388 filed Feb. 3, 2006. The contents of these applications are incorporated herein by reference in their entirety.

BACKGROUND OF THE INVENTION

1. Technical Field

The present invention relates to a compound.

2. Background Art

In the field of microfabrication represented by the manufacture of integrated circuit devices, lithographic technology enabling microfabrication with a line width of about 100 nm or less using an ArF excimer laser (wavelength: 193 nm), an $F_2$ excimer laser (wavelength: 157 nm), and the like has been demanded in order to increase the degree of integration in recent years. As a radiation-sensitive resin composition applicable to the excimer laser radiation, a number of chemically-amplified radiation-sensitive compositions utilizing a chemical amplification effect between a component having an acid-dissociable functional group and an acid generator, which is a component generating an acid upon irradiation, have been proposed. For example, a high molecular-weight compound for a photoresist comprising a resin component with a specific structure which contains a monomer unit having a norbornane ring derivative as a resin component is known (JP-A-2002-201232 and JP-A-2002-145955).

As a positive-tone photosensitive resin composition suitable for use with an exposure light source with a wavelength of 250 nm or less, particularly 220 nm or less, a resin in which an acid generating group, an alicyclic group, and an acid-dissociable group are introduced into the same molecule (JP-A-10-221852) and a photosensitive resin composition containing a sulfonium or iodonium salt resin which has a counter anion in the polymer chain in order to increase a photolysis efficiency (JP-A-9-325497) are known.

However, to achieve a higher degree of integration in the field of semiconductor, a radiation-sensitive resin composition used as a resist is required to possess more excellent resolution. In addition, along with the progress of microfabrication, there is a growing demand for wider focal depth allowance (hereinafter referred to as "DOF") and narrower line edge roughness (hereinafter referred to as "LER") of patterns. Along with progress of miniaturization in the semiconductor industry, development of a radiation-sensitive resin composition having excellent resolution and satisfying the demand of wide DOF and narrow LER is urgently need.

The resolution of the projection optical system provided in the projection aligner increases as the exposure wavelength used becomes shorter and the numerical aperture of the projection optical system becomes greater. Therefore, the exposure wavelength, which is a wavelength of radiation used in the projection aligner, has been reduced along with scaling down of integrated circuits year by year, and the numerical aperture of the projection optical system has been increased.

Depth of focus is as important as resolution in exposure. Resolution R and depth of focus δ are respectively shown by the following formulas.

$$R = k1 \cdot /NA \quad \text{(i)}$$

$$\delta = k2 \cdot /NA^2 \quad \text{(ii)}$$

wherein k is the exposure wavelength, NA is the numerical aperture of the projection optical system, and k2 and k2 are process coefficients. A short wavelength is advantageous to provide high resolution R, and a long wavelength is advantageous to provide a larger depth of focus δ.

A photoresist film is formed on the surface of an exposure target wafer, and the pattern is transferred to the photoresist film. In a general projection aligner, the space in which the wafer is placed is filled with air or nitrogen. When the space between the wafer and the lens of the projection aligner is filled with a medium having a refractive index of n, the numerical aperture NA is shown by the following formula.

$$NA = n \cdot \sin \theta \quad \text{(iii)}$$

wherein θ is an angle shown in FIG. 2. FIG. 2 shows the manner in which light is refracted with a lens, wherein 3 indicates a lens, 4 is an optical axis, 5 is a sample, and 6 shows the direction to which the light moves. D indicates a working distance.

From the formula (iii), it can be understood that a larger NA can be provided by using a liquid with n>1, whereby a high resolution R can be provided for the reason mentioned above.

Such a projection exposure method in which the space between a wafer and the lens of a projection aligner is filled with a medium with a refractive index n to transfer a more minute pattern is called a liquid immersion lithographic method. The liquid immersion lithographic method is considered to be an essential technology for lithography with reduced dimensions, particularly for lithography with dimensions of several ten nanometers.

In the liquid immersion lithography, a photoresist film applied and formed on a wafer and the lens of the projection aligner respectively come into contact with an immersion medium such as water. The immersion medium may permeate the photoresist film and reduces the photoresist resolution. Another problem is elution of a photoresist component into the immersion medium and pollution of the lens surface with such a photoresist component.

For these reasons, a photoresist film is demanded to maintain excellent liquid immersion resistance, without being eluted into an immersion medium such as water during the liquid immersion lithographic method, and the exposed area thereof is required to be easily dissolved in an alkaline solution used as a developer.

However, no radiation-sensitive resin composition has been produced which can produce a stable film against an immersion medium such as water during the liquid immersion lithographic method, exhibits excellent resolution, elutes only a minimal amount of acid generators, and produces an excellent pattern profile in the liquid immersion lithographic method.

SUMMARY OF THE INVENTION

According to one aspect of the present invention, a compound is represented by the following formula (5),

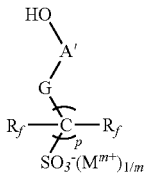

(5)

wherein at least one of $R_f$ groups represents a fluorine atom or a linear or branched perfluoroalkyl group having 1 to 10 carbon atoms, A' represents a substituted or unsubstituted, linear or branched alkylene group having 1 to 20 carbon atoms, an alkylene group having at least one hetero atom, or a single bond, G represents a divalent organic group having a fluorine atom or a single bond, $M^{m+}$ represents an onium cation, m represents a natural number of 1 to 3, and p represents a natural number of 1 to 8.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
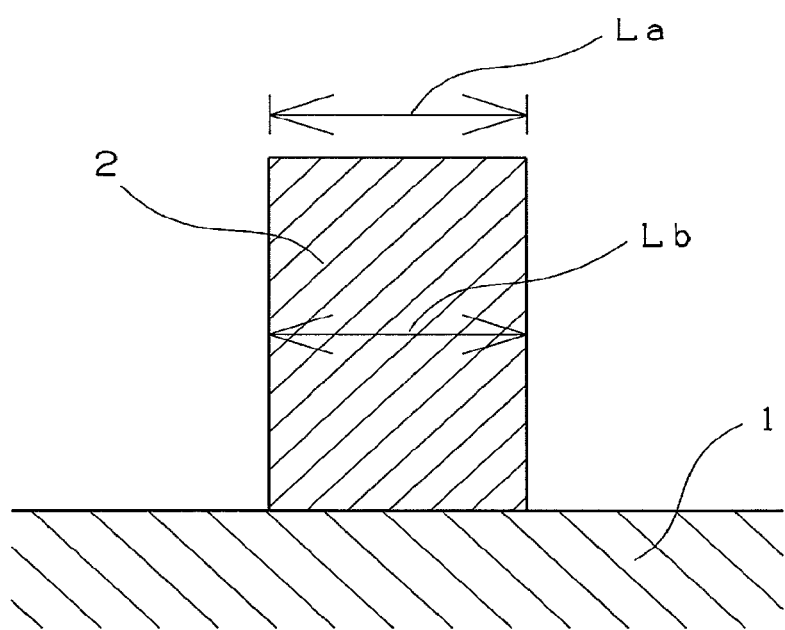
FIG. 1 is a cross-sectional view of a line- and space pattern.
Figure 2:
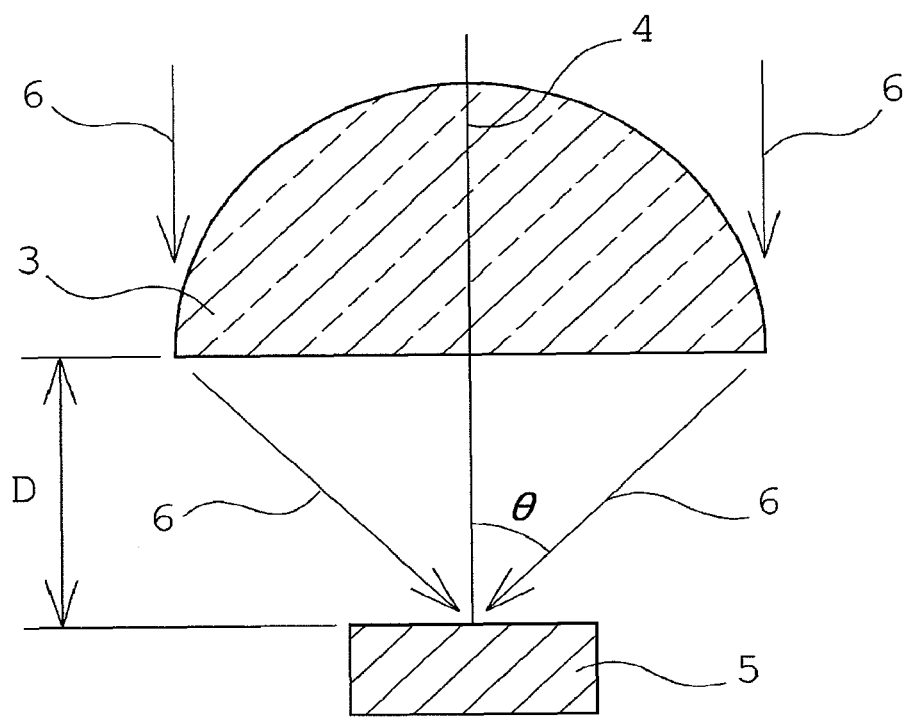
FIG. 2 is a diagram illustrative of mathematical formula (iii).

A novel compound of an embodiment of the present invention is shown by the following formula (1) or (2), which comprises an $—SO_3^-(M^{m+})_{1/m}$ group at the molecular terminal, or by the following formula (3).

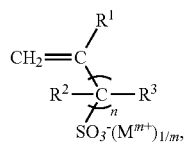

(1)

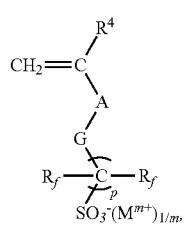

(2)

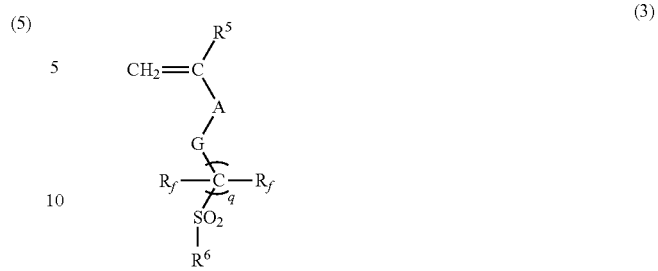

(3)

In the formula (1), $R^1$ is a methyl group, a trifluoromethyl group, or a hydrogen atom, $R^2$ and $R^3$ independently represent a hydrogen atom or a substituted or unsubstituted, linear or branched alkyl group having 1 to 10 carbon atoms, $M^{m+}$ represents a metal ion or an onium cation, m represents a natural number of 1 to 3, and n is a natural number of 0 to 3.

In the formula (2), $R^4$ is a methyl group, a trifluoromethyl group, or a hydrogen atom, at least one of $R_f$s represents a fluorine atom or a linear or branched perfluoroalkyl group having 1 to 10 carbon atoms, A represents a divalent organic group or a single bond, G represents a divalent organic group having a fluorine atom or a single bond, $M^{m+}$ represents a metal ion or an onium cation, m represents a natural number of 1 to 3, and p is a natural number of 1 to 8. In particular, A represents a —(CO)O-A'- group, wherein A' is a divalent hydrocarbon group, a divalent hydrocarbon group which contains at least one hetero atom, or a single bond.

In the formula (3), $R^5$ is a methyl group, a trifluoromethyl group, or a hydrogen atom, $R^6$ indicates a monovalent organic group, A represents a divalent organic group or a single bond, G represents a divalent organic group having a fluorine atom or a single bond, and q is a natural number of 1 to 8.

The polymer of the embodiment of the present invention can be prepared by copolymerizing monomers containing a monomer represented by the following formula (4).

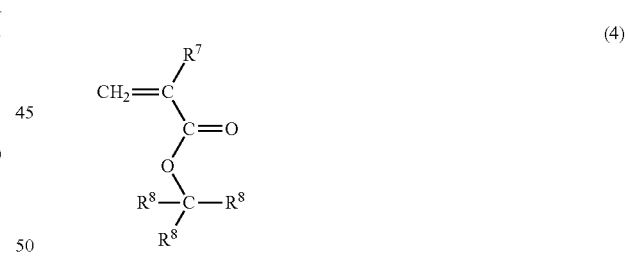

(4)

wherein $R^7$ represents a methyl group, a trifluoromethyl group, or a hydrogen atom, $R^8$ independently represents a monovalent alicyclic hydrocarbon group having 4 to 20 carbon atoms, a derivative thereof, or a linear or branched alkyl group having 1 to 4 carbon atoms, and (i) at least one of the $R^8$ groups is an alicyclic hydrocarbon group or a derivative thereof, or (ii) two of the $R^8$ groups form a divalent alicyclic hydrocarbon group having 4 to 20 carbon atoms or a derivative thereof in combination with the carbon atom to which the two $R^8$ groups bond.

[Compound Shown by the Formula (1)]

The compound shown by the formula (1) has a polymerizable unsaturated bond and an $—SO_3^-$ group at the position in which the unsaturated bond becomes a side chain after polymerization.

In the formula (1), $R^1$ represents a methyl group, a trifluoromethyl group, or a hydrogen atom.

$R^2$ and $R^3$ independently represent a hydrogen atom or a substituted or unsubstituted, linear or branched alkyl group having 1 to 10 carbon atoms. As examples of the substituted or unsubstituted, linear or branched alkyl group having 1 to 10 carbon atoms, linear alkyl groups such as a methyl group, an ethyl group, a propyl group, a butyl group, a pentyl group, a hexyl group, a heptyl group, an octyl group, a nonyl group, and a decyl group; and branched alkyl groups such as a 2-propyl group, a 2-butyl group, and a t-butyl group can be given. n is a natural number of 0 to 3. $M^{m+}$ will be described later.

[Compound Shown by the Formula (2)]

The compound shown by the formula (2) has a polymerizable unsaturated bond and has an $—SO_3^-$ group in a side chain in which a fluorine atom or a perfluoroalkyl group is bonded to the carbon atom on the α-position after the unsaturated bond has been polymerized.

In the formula (2), $R^4$ represents a methyl group, a trifluoromethyl group, or a hydrogen atom.

At least one of $R_f$s is a fluorine atom or a linear or branched perfluoroalkyl group having 1 to 10 carbon atoms.

As examples of the linear or branched perfluoroalkyl group having 1 to 10 carbon atoms, linear perfluoroalkyl groups such as a trifluoromethyl group, a pentafluoroethyl group, a heptafluoropropyl group, a nonafluorobutyl group, an undecafluoropentyl group, a tridecafluorohexyl group, a pentadecafluoroheptyl group, a heptadecafluorooctyl group, a nonadecafluorononyl group, and a heneicosadecyl group, and branched perfluoroalkyl groups such as a (1-trifluoromethyl) tetrafluoroethyl group, a (1-trifluoromethyl)hexafluoropropyl group, and a 1,1-bistrifluoromethyl-2,2,2-trifluoroethyl group can be given.

In the embodiment of the present invention, in order to provide excellent resolution, $R_f$ is preferably a fluorine atom or a trifluoromethyl group, and p is 1 or 2.

In the formula (2), A represents a divalent organic group or a single bond. As the divalent organic group, preferably a divalent hydrocarbon group, —O—, —(CO)O—, —O(CO)—, —CO—, an amide group, —SO₂—, —(CO)O-A'-, and the like can be given.

As preferable examples of divalent hydrocarbon groups, linear or cyclic hydrocarbon groups, which include saturated hydrocarbon groups, such as a methylene group, an ethylene group, a propylene group (a 1,3-propylene group, a 1,2-propylene group), a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an octadecamethylene group, a nonadecamethylene group, an icosylene group, a 1-methyl-1,3-propylene group, a 2-methyl-1,3-propylene group, a 2-methyl-1,2-propylene group, a 1-methyl-1,4-butylene group, a 2-methyl-1,4-butylene group, a methylidene group, ethylidene group, a propylidene group, and a 2-propylidene group; monocyclic hydrocarbon groups such as cycloalkylene groups having 3 to 10 carbon atoms such as cyclobutylene groups (e.g. a 1,3-cyclobutylene group), cyclopentylene groups (e.g. a 1,3-cyclopentylene group), cyclohexylene groups (e.g. a 1,4-cyclohexylene group), and cyclooctylene groups (e.g. a 1,5-cyclooctylene group); and bridged cyclic hydrocarbon groups such as cyclic hydrocarbon groups with 2 to 4 rings having 4 to 30 carbon atoms such as norbornylene groups (e.g. a 1,4-norbornylene group, a 2,5-norbornylene group), and adamantylene groups (e.g. a 1,5-adamantylene group, a 2,6-adamantylene group); and the like can be given.

As A' in the —(CO)O-A'- group, a divalent hydrocarbon group, a divalent hydrocarbon group which contains at least one hetero atom, or a single bond can be given.

As preferable examples of the divalent hydrocarbon group, chain-like or cyclic hydrocarbon groups can be given. Specific examples include saturated linear hydrocarbon groups such as a methylene group, an ethylene group, a propylene group (a 1,3-propylene group, a 1,2-propylene group), a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an octadecamethylene group, a nonadecamethylene group, an icosylene group, a 1-methyl-1,3-propylene group, a 2-methyl-1,3-propylene group, a 2-methyl-1,2-propylene group, a 1-methyl-1,4-butylene group, a 2-methyl-1,4-butylene group, a methylidene group, an ethylidene group, a propylidene group, and a 2-propylidene group; monocyclic hydrocarbon groups such as cycloalkylene groups having 3 to 10 carbon atoms such as cyclobutylene groups (e.g. a 1,3-cyclobutylene group), cyclopentylene groups (e.g. a 1,3-cyclopentylene group), cyclohexylene groups (e.g. a 1,4-cyclohexylene group), and cyclooctylene groups (e.g. a 1,5-cyclooctylene group); and bridged cyclic hydrocarbon groups such as cyclic hydrocarbon groups with 2 to 4 rings having 4 to 30 carbon atoms such as norbornylene groups (e.g. a 1,4-norbornylene group, a 2,5-norbornylene group), and adamanttylene groups (e.g. a 1,5-adamanttylene group, a 2,6-adamanttylene group).

As examples of the divalent hydrocarbon group which contains at least one hetero atom, an alkyleneoxyalkylene group, an alkylenesulfonylalkylene group, an alkylenethioalkylene group, an alkyleneoxycarbonylalkylene group, and an alkylenecarbonylalkylene group can be given.

As A, a —(CO)O-A'- group, a single bond, a methylene group, an ethylene group, and a norbornylene group are preferable. A single bond here indicates the case in which A does not exist in the formula (2).

As preferable examples of the —(CO)O-A'- group in the formula (5), —(CO)O—$CH_2CH_2CH_2CH_2$—, —(CO)O—$CH_2CH_2CH_2$—, —(CO)O—$CH_2CH_2$—, —(CO)O—CH($CH_3$)—, and —(CO)O—$CH_2CH_2$—O—$CH_2CH_2CH_2$— can be given.

In the formula (2), G indicates a divalent organic group having a fluorine atom. The divalent organic group having a fluorine atom is a hydrocarbon group in which all or some of the hydrogen atoms bonded to the carbon atoms of a divalent hydrocarbon group are substituted with fluorine atoms. As the divalent hydrocarbon group, a chain-like or branched hydrocarbon group is preferable.

As preferable examples of G, a difluoromethylene group and a tetrafluoroethylene group can be given.

As a combination of A and G, when G is a difluoromethylene group, A is preferably —(CO)O—, an ethylene group, or a single bond, and when G is a single bond, A is preferably —(CO)O—.

In the formula (1) or (2), $M^{m+}$ represents an onium cation.

As examples of the onium cation, a sulfonium cation, an iodonium cation, a phosphonium cation, a diazonium cation, an ammonium cation, and a pyridinium cation can be given.

Among these, the sulfonium cation represented by the following formula (1a) and the iodonium cation represented by the following formula (1b) are preferable.

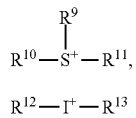

(1a)

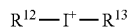

(1b)

$R^9$, $R^{10}$, and $R^{11}$ in the formula (1a) are independently a substituted or unsubstituted alkyl group having 1 to 10 carbon atoms or a substituted or unsubstituted aryl group having 6 to 18 carbon atoms, or any two or more of the $R^9$, $R^{10}$, and $R^{11}$ bond together with the sulfur atom in the formula to form a ring.

$R^{12}$ and $R^{13}$ in the formula (1b) independently represent a substituted or unsubstituted, linear or branched alkyl group having 1 to 10 carbon atoms, a substituted or unsubstituted aryl group having 6 to 18 carbon atoms, or $R^{12}$ and $R^{13}$ form a ring together with the iodine atom in the formula.

When $M^{m+}$ is copolymerized with a compound represented by the formula (4), $M^{m+}$ can be a metal ion. As a metal ion, alkali metal ions such as a sodium ion, a potassium ion, and a lithium ion, alkaline earth metal ions such as magnesium ion and a calcium ion, an iron ion, an aluminum ion, and the like can be given. Among these, the sodium ion, potassium ion, and lithium ion are preferable due to their capability of being easily ion-exchanged into sulfonate.

As examples of the unsubstituted, linear or branched alkyl group having 1 to 10 carbon atoms in the formula (1a) or (1b), a methyl group, an ethyl group, an n-propyl group, an i-propyl group, an n-butyl group, a 1-methylpropyl group, a 2-methylpropyl group, a t-butyl group, an n-pentyl group, an i-pentyl group, a 1,1-dimethylpropyl group, a 1-methylbutyl group, an n-hexyl group, an i-hexyl group, a 1,1-dimethylbutyl group, an n-heptyl group, an n-octyl group, an i-octyl group, a 2-ethylhexyl group, an n-nonyl group, and an n-decyl group can be given.

As examples of the substituents of the alkyl group, an aryl group having 6 to 30 carbon atoms, a linear, branched, or cyclic alkenyl group having 2 to 30 carbon atoms, and a group having 1 to 30 atoms containing a hetero atom such as a halogen atom, an oxygen atom, a nitrogen atom, a sulfur atom, a phosphorus atom, or a silicon atom can be given.

As examples of the substituted linear or branched alkyl group having 1 to 10 carbon atoms in the formula (1a) or (1b), a benzyl group, a methoxymethyl group, a methylthiomethyl group, an ethoxymethyl group, an ethylthiomethyl group, a phenoxymethyl group, a methoxycarbonylmethyl group, an ethoxycarbonylmethyl group, an acetylmethyl group, a fluoromethyl group, a trifluoromethyl group, a chloromethyl group, a trichloromethyl group, a 2-fluoropropyl group, a (trifluoroacetyl)methyl group, a (trichloroacetyl)methyl group, a (pentafluorobenzoyl)methyl group, an aminomethyl group, a (cyclohexylamino)methyl group, a (trimethylsilyl)methyl group, a 2-phenylethyl group, a 2-aminoethyl group, and a 3-phenylpropyl group can be given.

As examples of the unsubstituted aryl group having 6 to 18 carbon atoms in the formula (1a) or (1b), a phenyl group, a 1-naphthyl group, a 2-naphthyl group, a 1-anthryl group, and a 1-phenanthryl group can be given. As examples of the substituents of these aryl groups, a linear, branched, or cyclic alkyl group having 1 to 30 carbon atoms, and a group having 1 to 30 atoms containing a hetero atom such as a halogen atom, an oxygen atom, a nitrogen atom, a sulfur atom, a phosphorus atom, or a silicon atom can be given. As examples of the substituted aryl group having 6 to 18 carbon atoms, an o-tolyl group, a m-tolyl group, a p-tolyl group, a 4-hydroxyphenyl group, a 4-methoxyphenyl group, a mesityl group, an o-cumenyl group, a 2,3-xylyl group, a 2,4-xylyl group, a 2,5-xylyl group, a 2,6-xylyl group, a 3,4-xylyl group, a 3,5-xylyl group, a 4-fluorophenyl group, a 4-trifluoromethylphenyl group, a 4-chlorophenyl group, a 4-bromophenyl group, and a 4-iodophenyl group can be given.

A 5 to 7 member ring can be given as an example of the ring formed by bonding two or more of $R^9$, $R^{10}$, and $R^{11}$ in the formulas (1a) and (1b).

Specific examples of sulfonium cations or iodonium cations represented by the formula (1a) or (1b) are shown below.

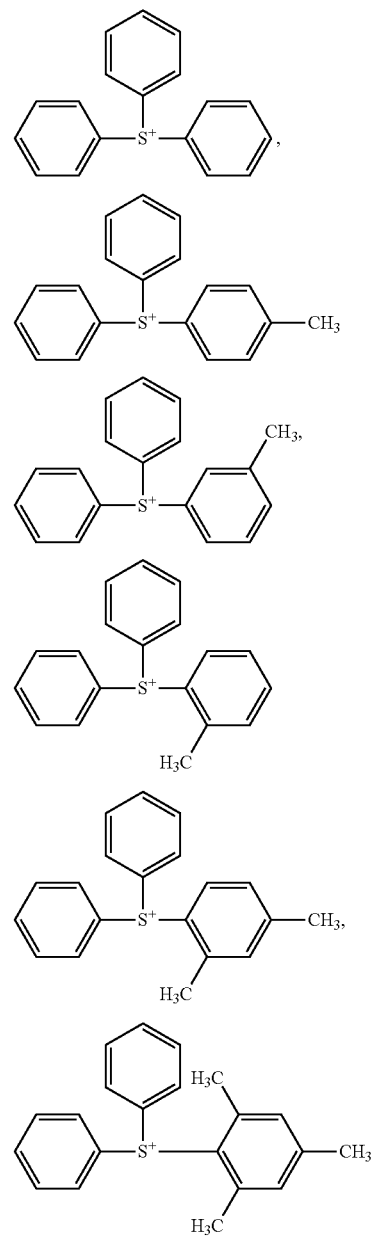

-continued
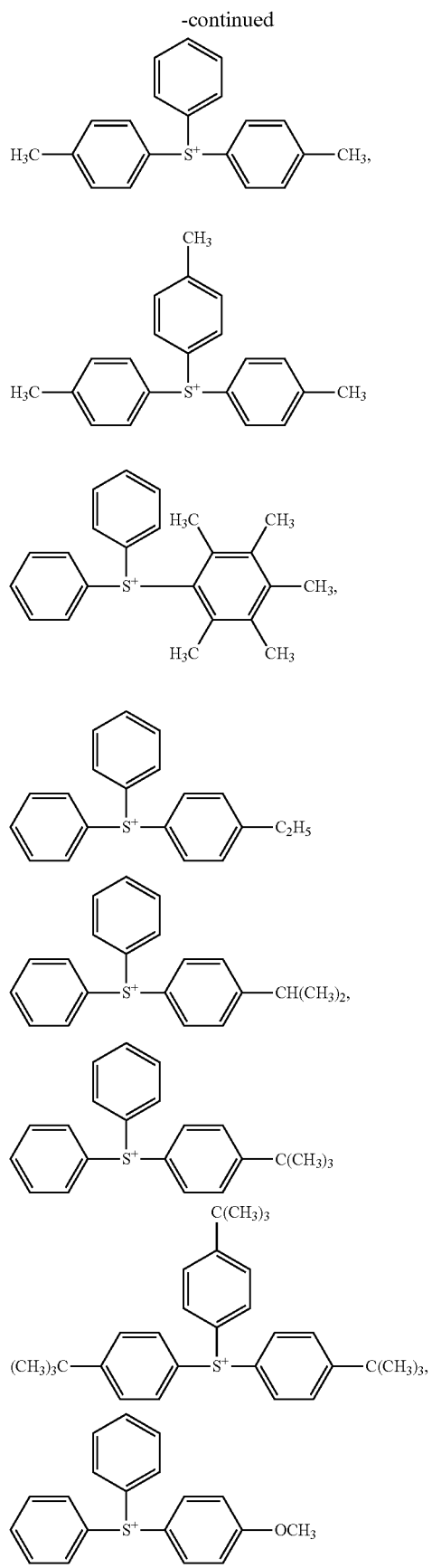
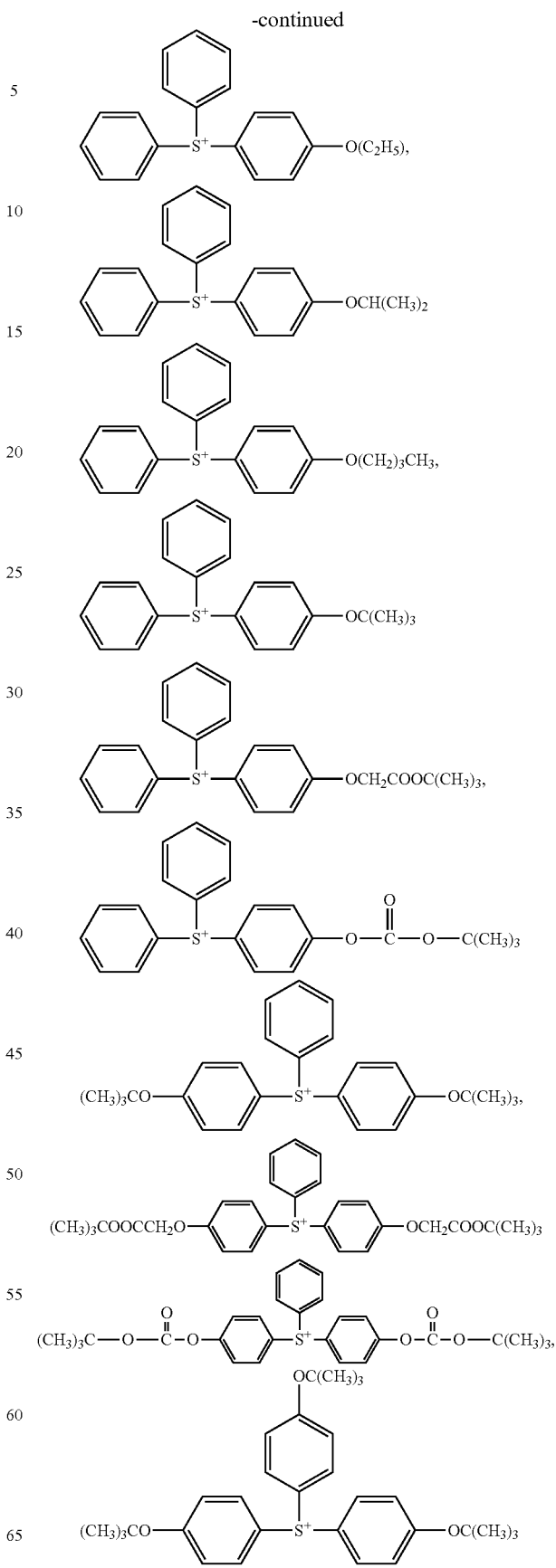

-continued

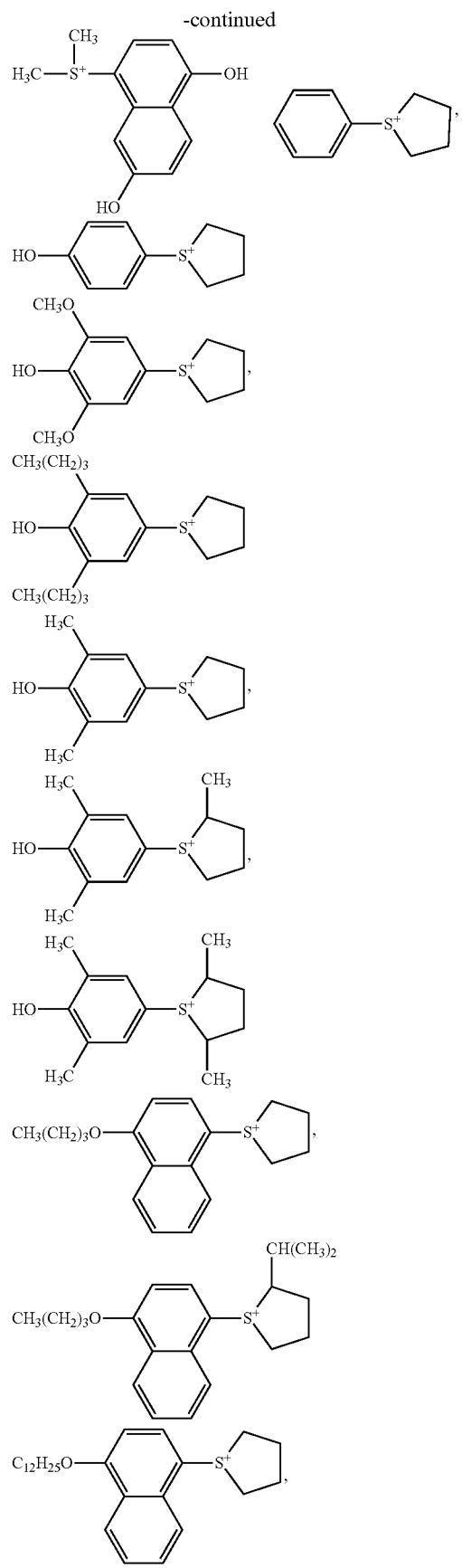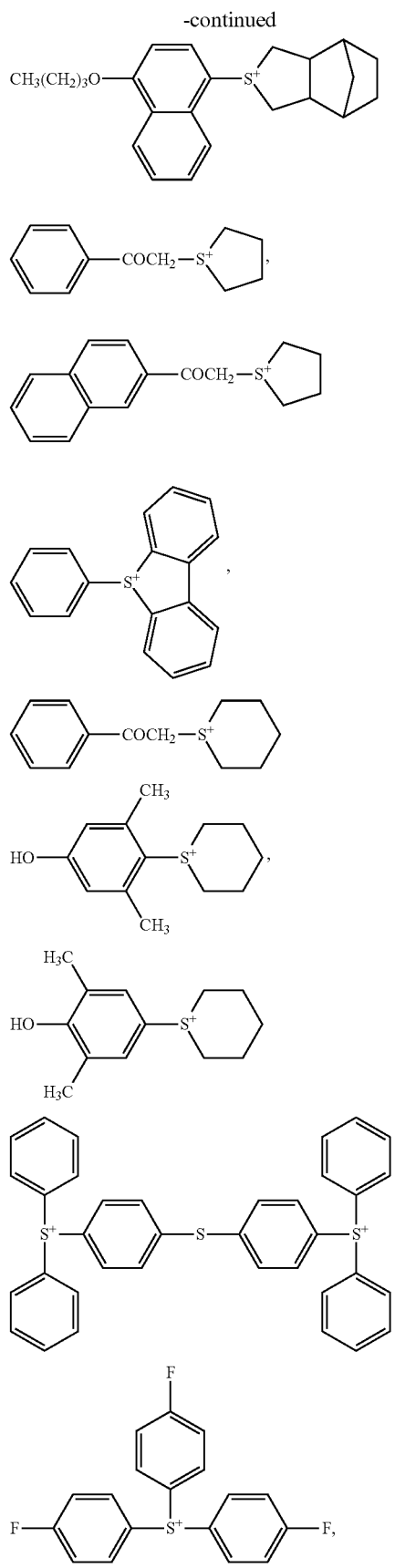

-continued
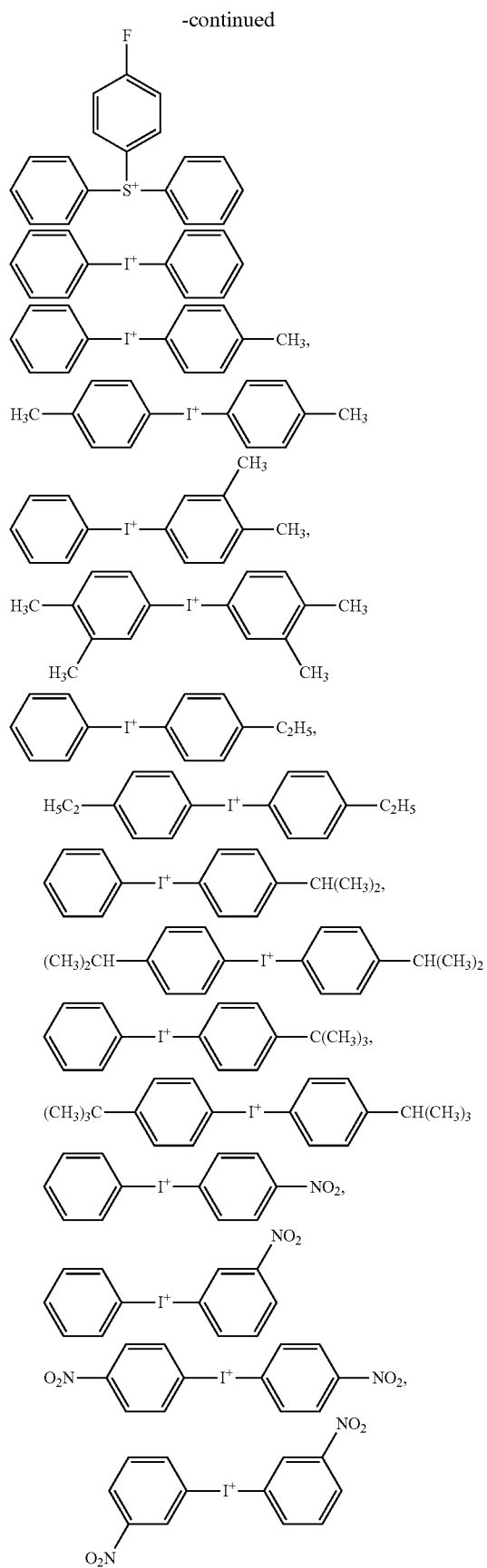
-continued
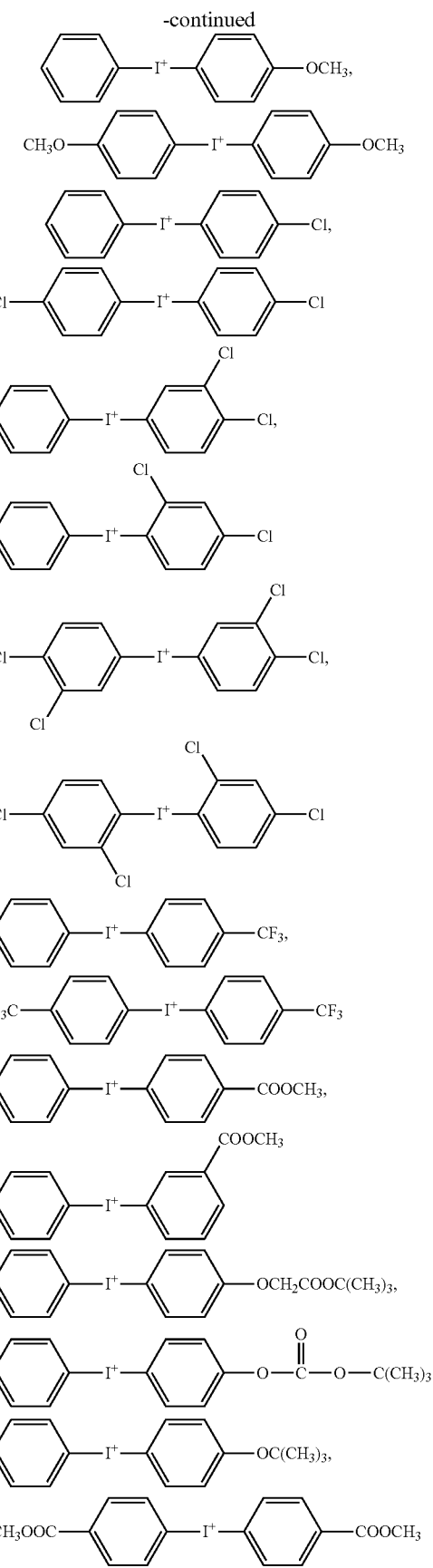

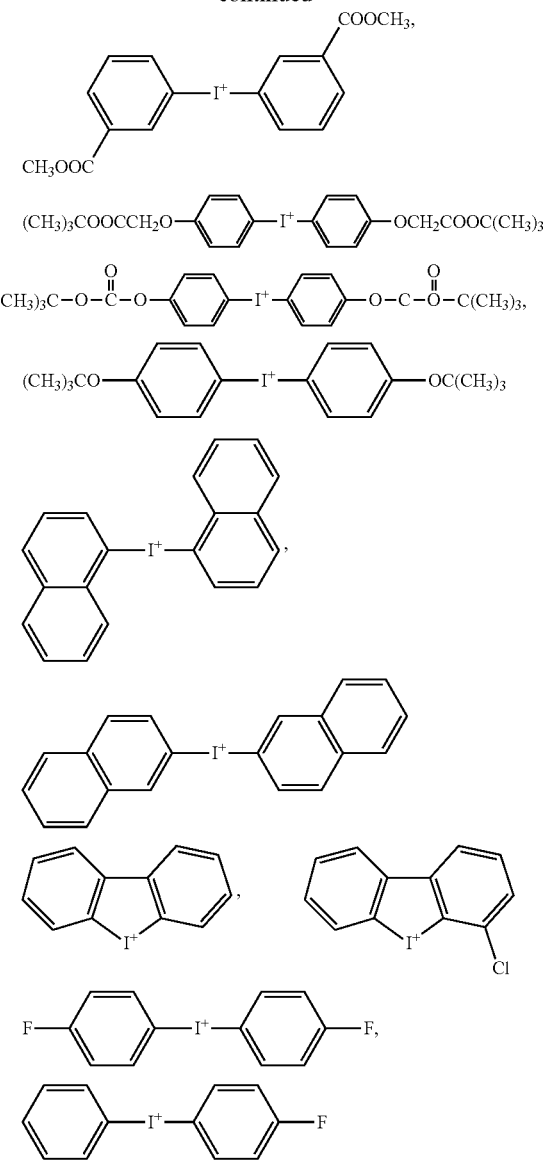
Specific examples of preferred compounds shown by the formula (1) or (2) are given below.
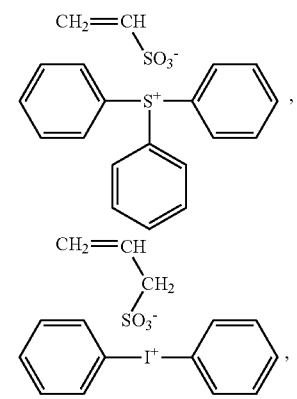
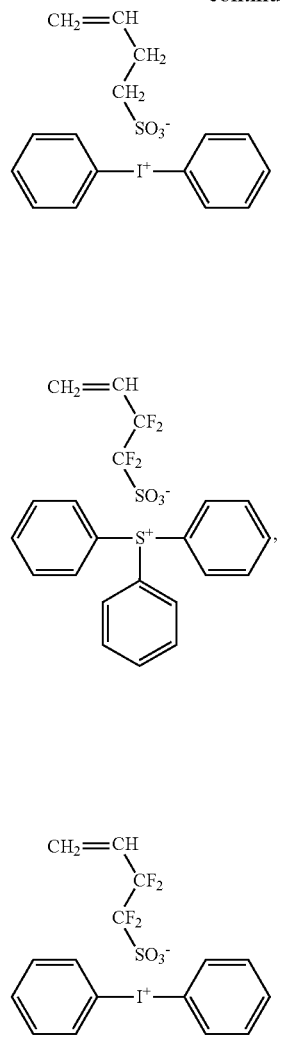

-continued

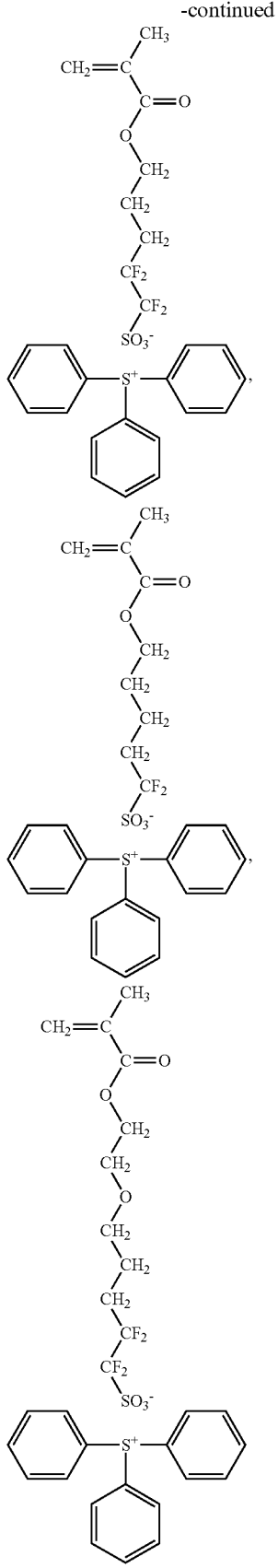

[Compound Shown by the Formula (3)]

The compound shown by the formula (3) has a polymerizable unsaturated bond and an —$SO_2$— group in the position in which the unsaturated bond becomes a side chain after polymerization. In the formula (3), $R^5$ represents a methyl group, a trifluoromethyl group, or a hydrogen atom.

A and G are respectively the same as A and G in the formula (2), and q indicates a natural number of 1 to 8.

$R^6$ represents a monovalent organic group. As the monovalent organic group, —$OR^6$ and —$R^{6'}$ can be given. As $R^{6'}$, a monovalent organic group shown by the following formula (3a) or (3b) can be given.

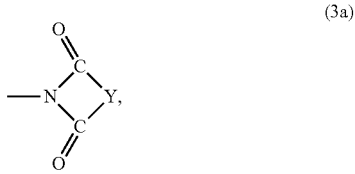

(3a)

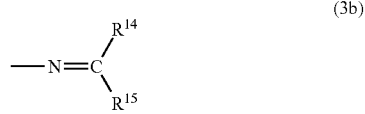

(3b)

In the formula (3a), Y represents a divalent organic group. In the formula (3b), $R^{14}$ and $R^{15}$ independently represent a hydrogen atom or a monovalent organic group, or form a ring together with the carbon atom to which $R^{14}$ and $R^{15}$ bond.

As examples of the divalent organic group represented by Y, a methylene group, a linear or branched alkylene group having 2 to 8 carbon atoms, a cycloalkylene group having 3 to 8 carbon atoms, a linear or branched alkenylene group having 2 to 8 carbon atoms, a cycloalkenylene group having 3 to 8 carbon atoms, an aralkylene group having 7 to 15 carbon atoms, an arylene group having 6 to 14 carbon atoms, a group originating from norbornane or its derivative, and a group originating from norbornene or its derivative can be given. As more specific examples, a 1,2-ethylene group, a trimethylene group, a 1,2-cyclohexylene group, an ethynylene group, a 1,2-diphenylethynylene group, a 1,2-cyclohexenylene group, a 1,2-phenylene group, a 4-chloro-1,2-phenylene group, a 4-nitro-1,2-phenylene group, a 4-methyl-1,2-phenylene group, a 4-methoxy-1,2-phenylene group, a 4-carboxy-1,2-phenylene group, a 1,8-naphthalene group, a 2,3-norbonanylene group, a 7-oxy-2,3-norbonanylene group, a 5,6-(2-norbonanylene) group, a 7-oxy-5,6-(2-norbonanylene) group, and the above-mentioned divalent organic groups having a substituent can be given.

Specific examples of preferable monovalent organic groups shown by the formula (3a) are given below.

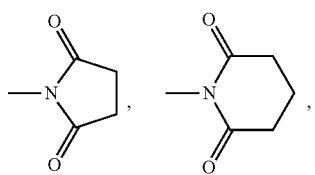

-continued

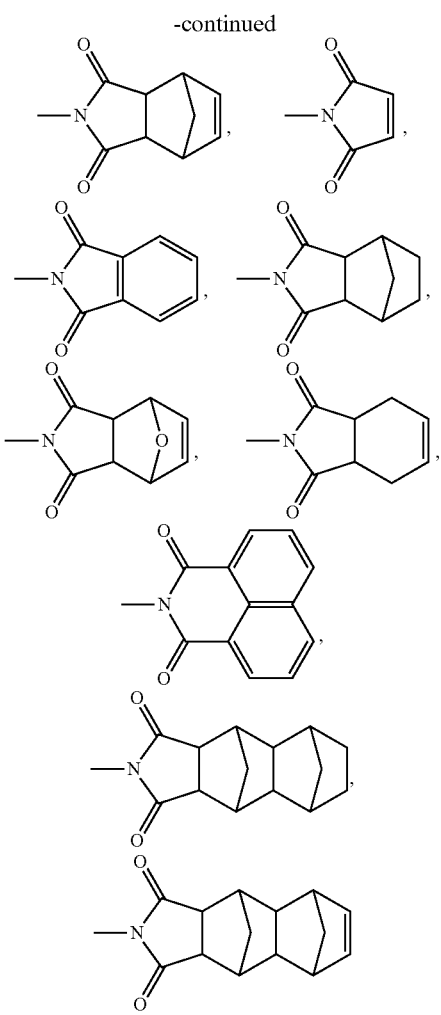

As the monovalent organic group represented by $R^{14}$ and $R^{15}$ in the formula (3b), a substituted or unsubstituted alkyl group having 1 to 20 carbon atoms, a substituted or unsubstituted aryl group, or a substituted or unsubstituted hatero-aryl group can be given.

The unsubstituted alkyl group having 1 to 20 carbon atoms may be linear, branched, or cyclic. As examples, a methyl group, an ethyl group, a propyl group, an isopropyl group, a butyl group, a t-butyl group, a pentyl group, an isopentyl group, a hexyl group, a 2-hexyl group, an isohexyl group, an n-octyl group, an s-octyl group, an n-dodecyl group, a cyclopropyl group, a cyclopentyl group, and a cyclohexyl group can be given. As a substituent of the substituted alkyl group, an aryl group, an alkenyl group, a cycloalkyl group, and an organic group containing a hetero atom such as a halogen atom, oxygen, nitrogen, sulfur, phosphorus, and silicon can be given. A substituted alkyl group is a group in which one or more hydrogen atoms bonded to the carbon atom of the above-mentioned unsubstituted alkyl group are replaced with these groups. As examples of the substituted alkyl group, a benzyl group, a methoxyethyl group, an acetylmethyl group, a methylthiomethyl group, an ethoxycarbonylmethyl group, a chloromethyl group, trichloromethyl group, a trifluoromethyl group, a 2-bromopropyl group, a trichloroacetylmethyl group, a trifluoroacetylmethyl group, a pentafluorobenzoyl-methyl group, a 2-phenylethyl group, a 3-phenylpropyl group, a cyclohexylaminomethyl group, an aminomethyl group, a 2-aminoethyl group, a phenoxymethyl group, a methoxymethyl group, a diphenylphosphinomethyl group, and a trimethylsilylmethyl group can be given.

As examples of the aryl group, a phenyl group, a naphthyl group, an anthryl group, and a phenanthryl group can be given. As examples of the hetero-aryl group, a thienyl group, a thianthrenyl group, a furyl group, a pyranyl group, a pyrrolyl group, a pyrazolyl group, an isothiazolyl group, an isooxazolyl group, a pyrazinyl group, a pyrimidinyl group, and a pyridazinyl group can be given. As a substituent of the substituted aryl group or the substituted hetero-aryl group, an alkyl group, haloalkyl group, and an organic group containing a hetero atom such as a halogen atom, oxygen, nitrogen, sulfur, phosphorus, and silicon can be given. As examples of the substituted aryl group, a p-methoxyphenyl group, an m-trifluorophenyl group, a p-tolyl group, a mesityl group, an o-cumenyl group, a 2,3-xylyl group, an o-bromophenyl group, an m-chlorophenyl group, a p-iodophenyl group, a 3-methoxythienyl group, and a 2-bromofuryl group can be given.

Some examples of the monovalent organic group shown by the formula (3b) are given below.

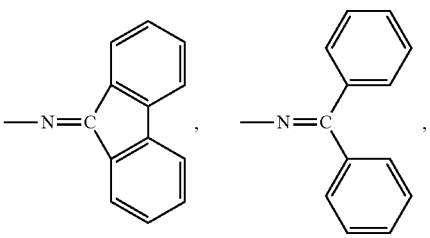

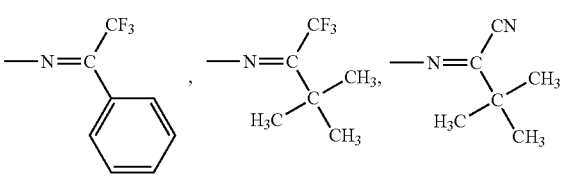

Specific examples of preferred compounds shown by the formula (3) are given below.

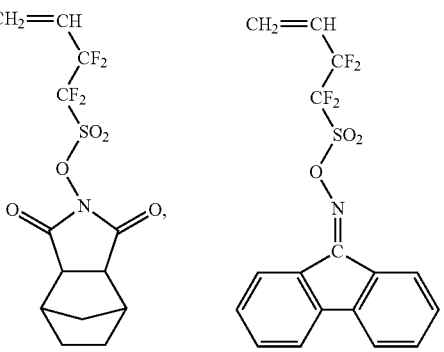

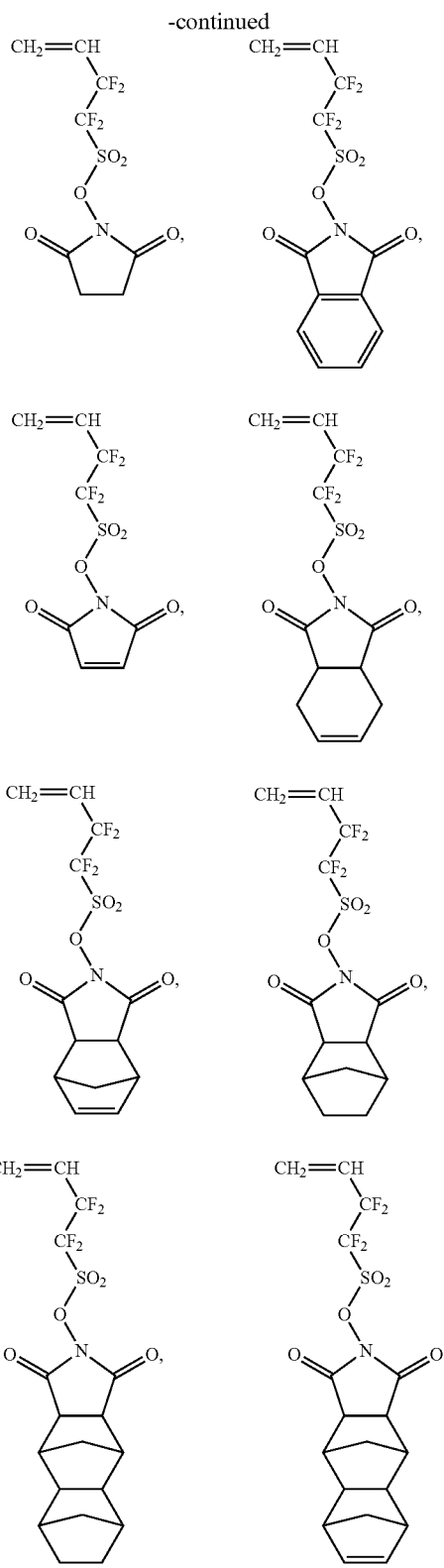

[Examples of Preparing Compounds Shown by the Formula (2) or (3)]

A compound shown by the formula (2) or (3) can be synthesized by the following method, for example.

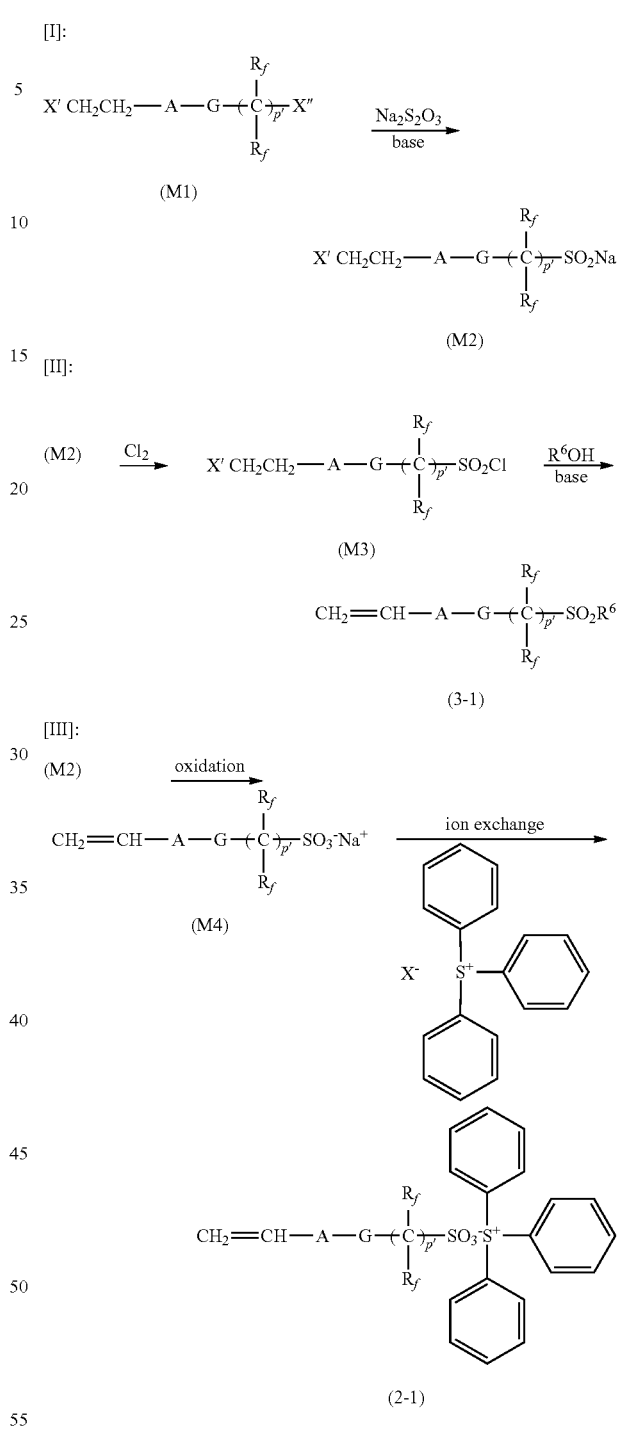

As shown in the reaction formulas [I] and [II], a corresponding precursor compound (M1) is reacted with sodium dithionite in the presence of an inorganic base to convert into sulfinate (M2), which is converted into a sulfonyl halide compound such as sulfonyl chloride (M3) using a halogenating agent such as chlorine gas. The sulfonyl halide compound is reacted with an N-hydroxyimide compound or an oxime compound in a reaction solvent in the presence of a base catalyst to produce a compound (3-1) shown by the formula (3).

As shown in the reaction formula [III], the sulfinate (M2) is oxidized to produce a counter ion exchange precursor of a sulfonate (M4), which is ion-exchanged to produce a compound (2-1) shown by the formula (2). Thus, the metallic ion of the sulfonate (M4) can be converted into an optional cation by an ion exchange reaction.

A, G, and $R_f$ in the formulas [I] and [II] are respectively the same as the A, G, and $R_f$ in the formula (2) or (3), and p' is p or q. As examples of the dissociable monovalent group for X' and X" in the precursor compound (M1), in addition to halogen atoms such as a chlorine atom, a bromine atom, and an iodine atom, a methanesulfonate group, a p-toluenesulfonate group, and the like can be given, with bromine and iodine atoms being preferable.

In the reaction of the precursor (M1) with sodium dithionite, the molar ratio of sodium dithionite to the precursor (M1) ($Na_2S_2O_3/M1$) is usually from 0.01 to 100 and preferably from 1.0 to 10.

As examples of the inorganic base used in the reaction, lithium carbonate, sodium carbonate, potassium carbonate, lithium hydrogencarbonate, sodium hydrogencarbonate, and potassium hydrogencarbonate can be given, with sodium hydrogencarbonate and potassium hydrogencarbonate being preferable.

The molar ratio of the inorganic base to the sodium dithionite (inorganic base/$Na_2S_2O_3$) is usually from 1.0 to 10.0, and preferably from 2.0 to 4.0.

This reaction is preferably carried out in a mixed solvent of an organic solvent and water. As the organic solvent, solvents possessing high mutual solubility with water such as lower alcohols, tetrahydrofuran, N,N-dimethylformamide, N,N-dimethylacetoamide, acetonitrile, and dimethylsulfoxide, and the like can be given, with N,N-dimethylacetoamide, acetonitrile, and dimethylsulfoxide being more preferable, and acetonitrile being particularly preferable.

The amount of the organic solvent used is usually from 5 to 100 parts by weight, preferably from 10 to 100 parts by weight, and particularly preferably from 20 to 90 parts by weight for 100 parts by weight of water.

The reaction is carried out at a temperature of usually from 40 to 200° C., and preferably from 60 to 120° C. for usually from 0.5 to 72 hours, and preferably from 2 to 24 hours. If the reaction temperature used is higher than the boiling point of the organic solvent or water, a pressure vessel such as an autoclave is used.

A method of bubbling chlorine gas into the reaction solution, for example, may be used for the reaction in the reaction formula [II].

Usually, an excessively large amount of a chlorinating agent for the amount of the sulfinate (M2) is used in the reaction.

This reaction is usually carried out in a reaction solvent. As the reaction solvent, water, organic solvents such as tetrahydrofuran, N,N-dimethylformamide, N,N-dimethylacetoamide, acetonitrile, dimethylsulfoxide, and the like can be given as preferable examples, with water, methanol, N,N-dimethylacetoamide, acetonitrile, and dimethylsulfoxide being more preferable, and water being particularly preferable.

The amount of the reaction solvent used is usually from 5 to 100 parts by weight, preferably from 10 to 100 parts by weight, and particularly preferably from 20 to 50 parts by weight for 100 parts by weight of the sulfinate (M2). If necessary, the above-mentioned organic solvent may be used together with water. In this case, the amount of the organic solvent used is usually from 5 to 100 parts by weight, preferably from 10 to 100 parts by weight, and particularly preferably from 20 to 90 parts by weight for 100 parts by weight of water.

The reaction is carried out at a temperature of usually from 0 to 100° C., preferably from 5 to 60° C., and particularly preferably from 5 to 40° C. for usually from five minutes to 12 hours, and preferably from 10 minutes to five hours.

In the reaction of sulfonyl chloride (M3) and a compound having an —OH group ($R^6OH$) such as an N-hydroxyimide compound or an oxime compound, the molar ratio of the N-hydroxyimide compound or the oxime compound to sulfonyl chloride (M3) is usually from 0.1 to 10.0, preferably from 0.3 to 5.0, and particularly preferably from 0.5 to 2.0.

This reaction is usually carried out in a reaction solvent. As the reaction solvent, acetonitrile, dimethyl formamide, tetrahydrofuran, dimethyl sulfoxide, methylene chloride, methylene bromide, and chloroform can be given as preferable examples, with acetonitrile, tetrahydrofuran, and methylene chloride being particularly preferable.

As the oxidizer used in the oxidation reaction of the sulfinate (M2) in the reaction formula [III], in addition to hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmium oxide (VII), ruthenium oxide (VII), sodium hypochlorite, sodium chlorite, oxygen gas, and ozone gas can be given, with hydrogen peroxide, methachloroperbenzoic acid, and t-butyl hydroperoxide being preferable.

The molar ratio of the oxidizer to the sulfinate (M2) is usually from 1.0 to 10.0 and preferably from 1.5 to 4.0. Furthermore, a transition metal catalyst may be used together with the oxidizer. As examples of the transition metal catalyst, disodium tungstate, iron (III) chloride, ruthenium (III) chloride, and selenium (IV) chloride can be given, with disodium tungstate being preferable.

The molar ratio of the transition metal catalyst to the sulfinate (M2) is usually from 0.001 to 2.0, preferably from 0.01 to 1.0, and particularly preferably from 0.03 to 0.5.

Furthermore, in addition to the above-mentioned oxidizer and transition metal catalyst, a buffer agent may be used for controlling the pH of the reaction solution.

As examples of the buffer agent, disodium hydrogenphosphate, sodium dihydrogenphosphate, dipotassium hydrogenphosphate, potassium dihydrogenphosphate, and the like can be given. The molar ratio of the buffer agent to the sulfinate (M2) is usually from 0.01 to 2.0, preferably from 0.03 to 1.0, and particularly preferably from 0.05 to 0.5.

This reaction is usually carried out in a reaction solvent. As the reaction solvent, water, organic solvents such as lower alcohols, tetrahydrofuran, N,N-dimethylformamide, N,N-dimethylacetoamide, acetonitrile, dimethylsulfoxide, acetic acid, trifluoroacetic acid, and the like can be given as preferable examples, with methanol, N,N-dimethylacetoamide, acetonitrile, and dimethylsulfoxide being more preferable, and methanol being particularly preferable.

The amount of the reaction solvent used is usually from 5 to 100 parts by weight, preferably from 10 to 100 parts by weight, and particularly preferably from 20 to 50 parts by weight for 100 parts by weight of the sulfinate (M2). If necessary, the organic solvent may be used together with water. In this case, the amount of the organic solvent used is usually from 5 to 100 parts by weight, preferably from 10 to 100 parts by weight, and particularly preferably from 20 to 90 parts by weight for 100 parts by weight of water.

The reaction is carried out at a temperature of usually from 0 to 100° C., preferably from 5 to 60° C., and particularly preferably from 5 to 40° C. for usually from 0.5 to 72 hours, and preferably from 2 to 24 hours.

The ion exchange reaction in the reaction formula [III] is carried out in a reaction solvent, for example. As the reaction solvent, water, organic solvents such as lower alcohols, tetrahydrofuran, N,N-dimethylacetoamide, acetonitrile, dimethylsulfoxide, and the like can be given as preferable examples, with water, methanol, N,N-dimethylacetoamide, acetonitrile, and dimethylsulfoxide being more preferable, and water being particularly preferable.

As examples of the monovalent anion for $X^-$ in the reaction formula [III], $F^-$, $Cl^-$, $Br^-$, $I^-$, perchlorate, hydrogen sulfurate, dihydrogen phosphorate, tetrafluorinated borate, aliphatic sulfonate, aromatic sulfonate, trifluoromethane sulfonate, fluorosulfonate, hexafluorinated phosphorate, and hexachlorinated antimonite can be given, with $Cl^-$, $Br^-$, hydrogen sulfurate, tetrafluorinated borate, and aliphatic sulfonate being preferable, and $Cl^-$, $Br^-$, and hydrogen sulfurate being particularly preferable. The molar ratio of the counter-ion exchange precursor to the sulfonate (M4) is usually from 0.1 to 10.0, preferably from 0.3 to 4.0, and particularly preferably from 0.7 to 2.0. The amount of the reaction solvent used is usually from 100 to 1,000 parts by weight, preferably from 200 to 900 parts by weight, and more preferably from 200 to 600 parts by weight for 100 parts by weight of the sulfonate (M4). If necessary, the organic solvent may be used together with water. In this case, the amount of the organic solvent used is usually from 5 to 100 parts by weight, preferably from 10 to 100 parts by weight, and more preferably from 20 to 90 parts by weight for 100 parts by weight of water. The reaction is usually carried out at a temperature of from 0 to 80° C., and preferably from 5 to 30° C. for usually from 10 minutes to six hours, and preferably from 30 minutes to two hours.

A method such as ion exchange chromatography may be used for the ion exchange reaction. As examples of the ion exchange resin, QAE-Sephadex A-25 and QAE-Sephadex A-50 can be given. As examples of the developing solvent, a lower alcohol, tetrahydrofuran, N,N-dimethylacetamide, acetonitrile, and dimethylsulfoxide can be given.

The onium sulfonate compound (2-1) prepared in this manner can be purified by extraction with an organic solvent.

As the organic solvent used for purification, organic solvents that do not mix with water are preferable. Examples include esters such as ethyl acetate and n-butyl acetate, ethers such as diethyl ether, and halogenated alkyls such as methylene chloride and chloroform.

In the embodiment of the present invention, the sulfonate (M4) of a counter-ion exchange precursor is useful as a compound of the formula (3-1) which generates a sulfonic acid by the effect of light, and a sulfonyl halide compound having a polymerizable unsaturated bond prepared by dehalogenation of the sulfonyl chloride (M3) is useful as a compound shown by the formula (3-1) which generates sulfonic acid by the effect of light.

Among the compounds shown by the formula (2), the compound A shown by the formula —(CO)O-A'- can be synthesized by the following method, for example.

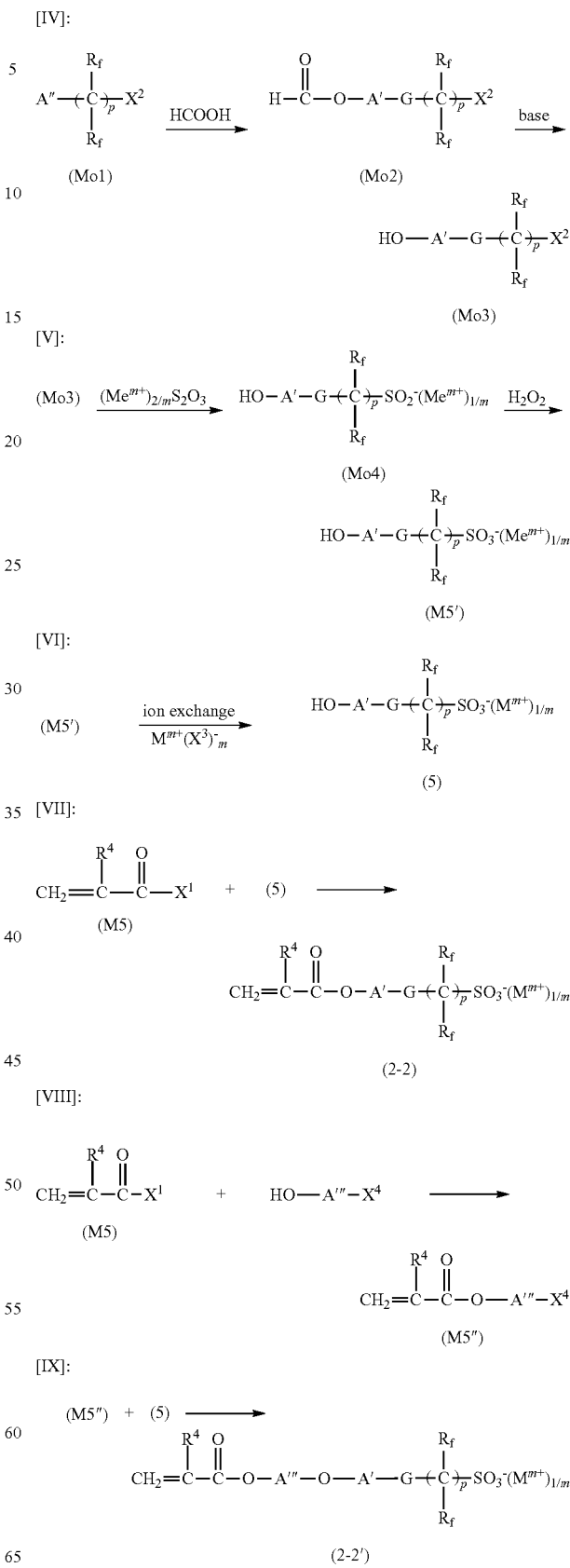

As shown in the reaction formulas [IV], [V], and [VI], a precursor compound (M02) can be prepared by the addition reaction of formic acid with a precursor compound (M01) which has a double bond in the A" area. A precursor compound (M03) can be prepared by treating the precursor compound (M02) with a base. A precursor compound (M04) can be prepared by reacting the precursor compound (M03) with a metal salt of dithionous acid. A compound shown by the formula (M5'), which has a metal salt sulfonic acid and a hydroxyl group at the molecular terminals can be prepared by treating the precursor compound (M04) with an acid, and a compound shown by the formula (5) can be prepared by an ion-exchange reaction.

As shown in the reaction formula [VII], a compound shown by the formula (2) in which A is —(CO)O-A'- (a compound of the formula (2-2)) can be prepared by reacting the compound shown by the formula (5) and the compound shown by the formula (M5).

A compound shown by the formula (M5') before the ion-exchange reaction can also be used as an intermediate material of the compound shown by the formula (2) of the embodiment of the present invention.

When A' is a divalent hydrocarbon group containing a hetero atom, as shown in the reaction formula [VIII] and [IX], after reacting the compound shown by the formula (M5) with a halogenated alcohol (HO-A'''-$X^4$), a compound (2-2') shown by the formula (2) which contains a hetero atom in a side chain can be prepared according to the same reaction as that shown by the reaction formula [VII].

A', G, $R_f$, $X^1$, M, m, and p in the formulas [IV], [V], [VI], and [VII] are respectively the same as those in the formulas (2), (M5), and (5). A''' represents an alkylene group. $X^2$, $X^3$, and $X^4$ represent dissociable monovalent substituents. As examples of the dissociable monovalent substituents represented by $X^2$, $X^3$, and $X^4$, halogen atoms such as a chlorine atom, a bromine atom, and an iodine atom; a methanesulfonate group; and a p-toluenesulfonate group can be given.

In the reaction of the precursor (M01) with formic acid (HCOOH) according to the reaction formula [IV]), the molar ratio of formic acid to the precursor (M01) is usually from 1 to 100, and preferably from 5 to 20. This reaction is preferably carried out without using a solvent or in water or an organic solvent such as dichloromethane and chloroform, and more preferably without using a solvent or in water. A strong acid such as perchloric acid can also be used as a catalyst. The molar ratio of the strong acid to the precursor compound (M01) is usually from 0.01 to 10, and preferably from 0.1 to 3. The reaction is carried out at a temperature of usually from 0 to 200° C., and preferably from 40 to 110° C. for usually from 0.3 to 72 hours, and preferably from 0.5 to 12 hours.

As examples of the base used in the hydrolysis reaction of formate (M02) and a base, lithium carbonate, sodium carbonate, potassium carbonate, lithium hydrogencarbonate, sodium hydrogencarbonate, and potassium hydrogencarbonate can be given, with sodium carbonate and potassium carbonate being preferable.

The molar ratio of the base to the formate (M02) is usually from 0.1 to 10, and preferably from 1 to 3. This reaction is preferably carried out in water or a polar solvent such as an alcohol, preferably in water or methanol. The reaction is carried out at a temperature of usually from 0 to 200° C., and preferably from 20 to 100° C. for usually from 0.5 to 72 hours, and preferably from 1 to 24 hours.

In the reaction formula [V], $M_e^{m+}$ represents a metal ion. In the reaction of the precursor compound (M03) with a metal salt of dithionous acid according to the reaction formula [V], the molar ratio of the metal salt of dithionous acid to the precursor compound (M03) is usually from 0.01 to 100, and preferably from 1.0 to 10. As examples of the inorganic base used in the reaction, lithium carbonate, sodium carbonate, potassium carbonate, lithium hydrogencarbonate, sodium hydrogencarbonate, and potassium hydrogencarbonate can be given, with sodium hydrogencarbonate and potassium hydrogencarbonate being preferable. The molar ratio of the inorganic base to the metal salt of dithionous acid is usually from 1.0 to 10.0, and preferably from 2.0 to 4.0. This reaction is preferably carried out in a mixed solvent of an organic solvent and water. As the organic solvent, solvents possessing high mutual solubility with water such as lower alcohols, tetrahydrofuran, N,N-dimethylformamide, N,N-dimethylacetoamide, acetonitrile, and dimethylsulfoxide, and the like can be given, with N,N-dimethylacetoamide, acetonitrile, and dimethylsulfoxide being more preferable, and acetonitrile being particularly preferable. The amount of the organic solvent used is usually from 5 to 100 parts by weight, preferably from 10 to 100 parts by weight, and particularly preferably from 20 to 90 parts by weight for 100 parts by weight of water. The reaction is carried out at a temperature of usually from 40 to 200° C., and preferably from 60 to 120° C. for usually from 0.5 to 72 hours, and preferably from 2 to 24 hours. If the reaction temperature used is higher than the boiling point of the organic solvent or water, a pressure vessel such as an autoclave is used.

As the oxidizer used in the oxidation reaction of the sulfinate (M04) in the reaction formula [V], in addition to hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmium oxide (VII), ruthenium oxide (VII), sodium hypochlorite, sodium chlorite, oxygen gas, and ozone gas can be given, with hydrogen peroxide, methachloroperbenzoic acid, and t-butyl hydroperoxide being preferable.

The molar ratio of the oxidizer to the sulfinate (M04) is usually from 1.0 to 10.0, and preferably from 1.5 to 4.0. Furthermore, a transition metal catalyst may be used together with the oxidizer. As examples of the transition metal catalyst, disodium tungstate, iron (III) chloride, ruthenium (III) chloride, and selenium (IV) chloride can be given, with disodium tungstate being preferable. The molar ratio of the transition metal catalyst to the sulfinate (M04) is usually from 0.001 to 2.0, preferably from 0.01 to 1.0, and particularly preferably from 0.03 to 0.5.

Furthermore, in addition to the above-mentioned oxidizer and transition metal catalyst, a buffer agent may be used for controlling the pH of the reaction solution.

As examples of the buffer agent, disodium hydrogenphosphate, sodium dihydrogenphosphate, dipotassium hydrogenphosphate, potassium dihydrogenphosphate, and the like can be given. The molar ratio of the buffer agent to the sulfinate (M04) is usually from 0.01 to 2.0, preferably from 0.03 to 1.0, and particularly preferably from 0.05 to 0.5.

This reaction is usually carried out in a reaction solvent. As the reaction solvent, water, organic solvents such as lower alcohols, tetrahydrofuran, N,N-dimethylformamide, N,N-dimethylacetoamide, acetonitrile, dimethylsulfoxide, acetic acid, trifluoroacetic acid, and the like can be given as preferable examples, with methanol, N,N-dimethylacetoamide, acetonitrile, and dimethylsulfoxide being more preferable, and methanol being particularly preferable. The amount of the reaction solvent used is usually from 5 to 100 parts by weight, preferably from 10 to 100 parts by weight, and particularly preferably from 20 to 50 parts by weight for 100 parts by weight of the sulfinate (M04). If necessary, the organic solvent may be used together with water. In this case, the amount of the organic solvent used is usually from 5 to 100 parts by weight, preferably from 10 to 100 parts by weight, and particularly preferably from 20 to 90 parts by weight for 100 parts by weight of water. The reaction is carried out at a temperature of usually from 0 to 100° C., preferably from 5 to 60° C., and more preferably from 5 to 40° C. for usually from 0.5 to 72 hours, and preferably from 2 to 24 hours.

The ion exchange reaction in the reaction formula [VI] is carried out in a reaction solvent, for example. As the reaction solvent, water, organic solvents such as lower alcohols, tetrahydrofuran, N,N-dimethylacetoamide, acetonitrile, dimethylsulfoxide, and the like can be given as preferable examples, with water, methanol, N,N-dimethylacetoamide, acetonitrile, and dimethylsulfoxide being more preferable, and water being particularly preferable. In the reaction formula [VI], $M^{m+}$ represents an onium cation.

The molar ratio of the counter-ion exchange precursor (M5') to the $M^{m+}(X^3)^-_m$ is usually from 0.1 to 10.0, preferably from 0.3 to 4.0, and more preferably from 0.7 to 2.0. The amount of the reaction solvent used is usually from 100 to 1,000 parts by weight, preferably from 200 to 900 parts by weight, and more preferably from 200 to 600 parts by weight for 100 parts by weight of the counter ion exchange precursor (M5'). If necessary, the organic solvent may be used together with water. In this case, the amount of the organic solvent used is usually from 5 to 100 parts by weight, preferably from 10 to 100 parts by weight, and more preferably from 20 to 90 parts by weight for 100 parts by weight of water. The reaction is usually carried out at a temperature of from 0 to 80° C., and preferably from 5 to 30° C. for usually from 10 minutes to six hours, and preferably from 30 minutes to two hours.

A method such as ion exchange chromatography may be used for the ion exchange reaction. As examples of the ion exchange resin, QAE-Sephadex A-25 and QAE-Sephadex A-50 can be given. As examples of the developing solvent, a lower alcohol, tetrahydrofuran, N,N-dimethylacetamide, acetonitrile, and dimethylsulfoxide can be given.

The compound shown by the formula (5) of the embodiment of the present invention is preferably synthesized via a sulfonate (M04) prepared by the reaction formula [V] and an intermediate of a counter ion exchange precursor (M5') which is prepared by oxidizing the sulfonate (M04).

The onium sulfonate compound (5) prepared in this manner can also be purified by extraction using an organic solvent.

As the organic solvent used for purification, organic solvents that do not mix with water are preferable. Examples include esters such as ethyl acetate and n-butyl acetate, ethers such as diethyl ether, and halogenated alkyls such as methylene chloride and chloroform.

[Polymer]

The polymer of the embodiment of the present invention can be prepared by polymerizing a monomer or a monomer mixture containing the above compound (1), (2), or (3). The polymer can also be prepared by copolymerizing a monomer containing the compound represented by the following formula (4).

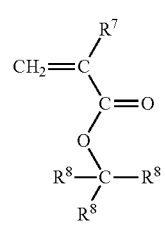

wherein $R^7$ represents a methyl group, a trifluoromethyl group, or a hydrogen atom, $R^8$ independently represents a monovalent alicyclic hydrocarbon group having 4 to 20 carbon atoms, a derivative thereof, or a linear or branched alkyl group having 1 to 4 carbon atoms, provided that at least one of the $R^8$ groups is an alicyclic hydrocarbon group or a derivative thereof, or two of the $R^8$ groups form a divalent alicyclic hydrocarbon group having 4 to 20 carbon atoms or a derivative thereof in combination with the carbon atom to which the two $R^8$ groups bond, with the remaining $R^8$ group being a linear or branched alkyl group having 1 to 4 carbon atoms, a monovalent alicyclic hydrocarbon group having 4 to 20 carbon atoms, or a derivative thereof.

As examples of the monovalent alicyclic hydrocarbon group having 4 to 20 carbon atoms and the divalent alicyclic hydrocarbon group having 4 to 20 carbon atoms formed by two $R^8$ groups, alicyclic groups derived from a cycloalkane such as norbornane, tricyclodecane, tetracyclododecane, adamantane, cyclobutane, cyclopentane, cyclohexane, cycloheptane, or cyclooctane, and groups prepared by replacing hydrogen atoms on these alicyclic groups with one or more linear, branched, or cyclic alkyl groups having 1 to 4 carbon atoms, such as a methyl group, an ethyl group, an n-propyl group, an i-propyl group, an n-butyl group, a 2-methylpropyl group, a 1-methylpropyl group, and a t-butyl group can be given. Of these alicyclic hydrocarbon groups, an alicyclic group derived from norbornane, tricyclodecane, tetracyclododecane, adamantane, cyclopentane, or cyclohexane, a group in which such an alicyclic ring is substituted with any one of the above alkyl groups, and the like are preferable.

As examples of derivatives of the above alicyclic hydrocarbon groups, groups having one or more substituents such as a hydroxyl group; a carboxyl group; an oxo group (=O), a hydroxyalkyl group having 1 to 4 carbon atoms such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, and a 4-hydroxybutyl group; an alkoxyl group having 1 to 4 carbon atoms such as a methoxy group, an ethoxy group, an n-propoxy group, an i-propoxy group, an n-butoxy group, a 2-methylpropoxy group, a 1-methylpropoxy group, and a t-butoxy group; a cyano group; a cyanoalkyl group having 2 to 5 carbon atoms such as a cyanomethyl group, a 2-cyanoethyl group, a 3-cyanopropyl group, and a 4-cyanobutyl group; and the like can be given. Of these substituents, a hydroxyl group, a carboxyl group, a hydroxymethyl group, a cyano group, a cyanomethyl group, and the like are preferable.

As examples of the linear or branched alkyl group having 1 to 4 carbon atoms represented by $R^8$, a methyl group, an ethyl group, an n-propyl group, an i-propyl group, an n-butyl group, a 2-methylpropyl group, a 1-methylpropyl group, and a t-butyl group can be given. Of these alkyl groups, a methyl group and an ethyl group are preferable.

The group —COOC(R$^8$)$_3$ in the formula (4) is a group which dissociates by the action of an acid and produces a carboxyl group. As examples of the —C(R$^8$)$_3$ part in the —COOC(R$^8$)$_3$ group, groups shown by the formulas (4a), (4b), (4c), or (4d) can be given.

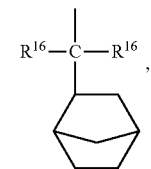
(4a)

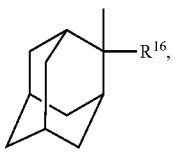
(4b)

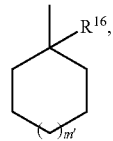
(4c)

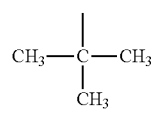
(4d)

In the formulas (4a), (4b), and (4c), R$^{16}$ independently represents a linear or branched alkyl group having 1 to 4 carbon atoms and m' indicates 0 or 1.

As examples of the linear or branched alkyl group having 1 to 4 carbon atoms represented by R$^{16}$, a methyl group, an ethyl group, an n-propyl group, an i-propyl group, an n-butyl group, a 2-methylpropyl group, a 1-methylpropyl group, and a t-butyl group can be given. Of these alkyl groups, a methyl group and an ethyl group are preferable.

Among the groups shown by the formula (4a), a group having a methyl group for both of the two R$^{16}$ is preferable. Among the groups shown by the formula (4b), groups having a methyl group or an ethyl group for R$^{16}$ are preferable. Among the groups shown by the formula (4c), a group in which m' is 0 and R$^{16}$ is a methyl group, a group in which m' is 0 and R$^{16}$ is an ethyl group, a group in which m' is 1 and R$^{16}$ is a methyl group, and a group in which m' is 1 and R$^{16}$ is an ethyl group are preferable.

Specific examples of the groups shown by the formulas (4a), (4b), and (4c) are given below.

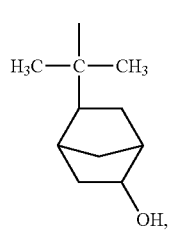 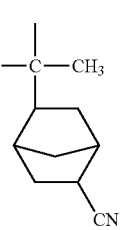 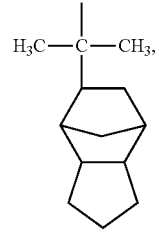

-continued

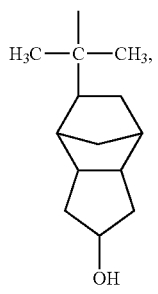 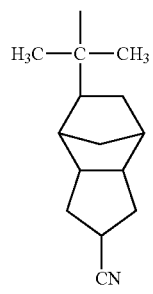 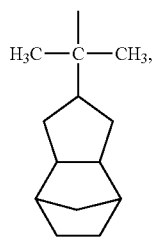

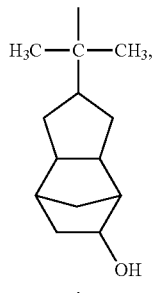 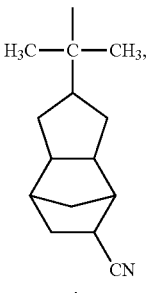 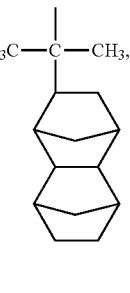

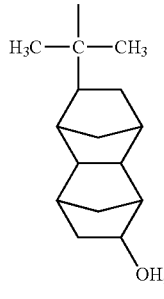 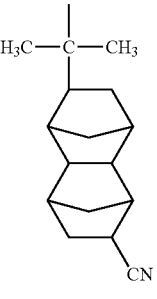 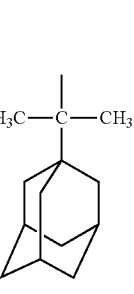

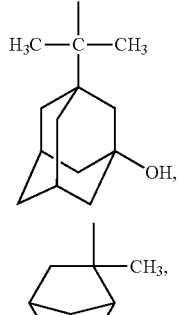 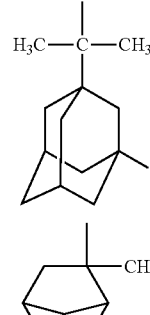 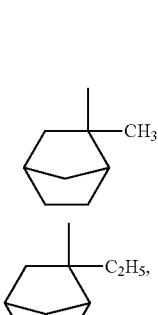

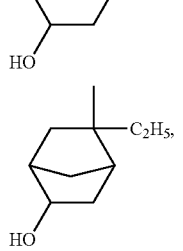 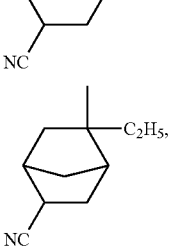 

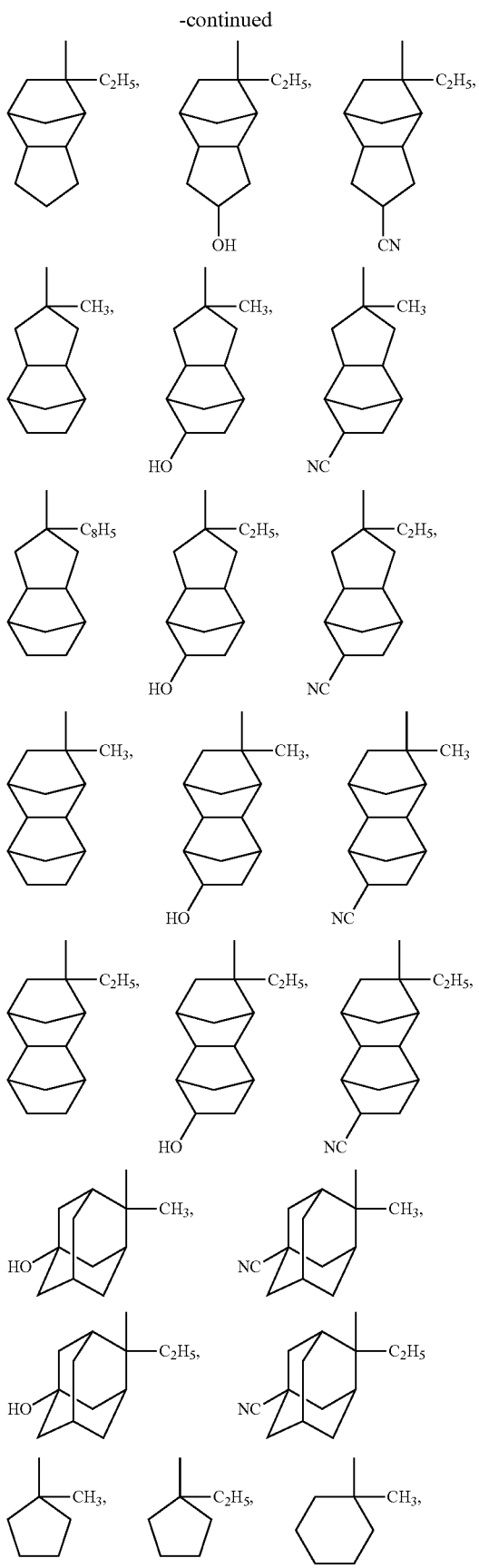

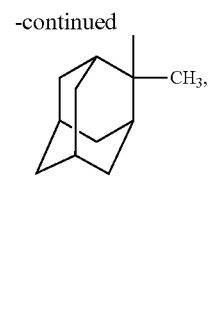

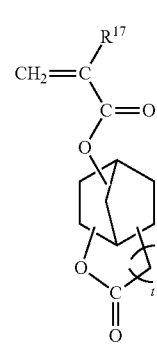

The polymer of the embodiment of the present invention may further comprise other compounds as monomers to be copolymerized. As the other compounds, the compounds shown by the following formula (6) are preferably included as monomers.

$$\underset{(6)}{CH_2=C\underset{|}{\overset{R^{17}}{\underset{C=O}{|}}}}$$

In the formula (6), $R^{17}$ represents a hydrogen atom, a methyl group, or a trifluoromethyl group, and t indicates 0 or 1.

Examples of the other compounds include monofunctional compounds, such as (meth)acrylates having a bridged hydrocarbon skeleton such as norbornyl(meth)acrylate, isonorbornyl(meth)acrylate, tricyclodecanyl(meth)acrylate, tetracyclodecanyl(meth)acrylate, dicyclopentenyl(meth)acrylate, adamantyl(meth)acrylate, and adamantylmethyl (meth)acrylate; carboxyl group-containing esters having a bridged hydrocarbon skeleton of an unsaturated carboxylic acid such as carboxynorbornyl(meth)acrylate, carboxytricyclodecanyl (meth)acrylate, and carboxytetracyclodecanyl(meth)acrylate;

(meth)acrylates having no bridged hydrocarbon skeleton such as methyl (meth)acrylate, ethyl(meth)acrylate, n-propyl (meth)acrylate, n-butyl(meth)acrylate, 2-methylpropyl (meth)acrylate, 1-methylpropyl(meth)acrylate, t-butyl(meth) acrylate, 2-hydroxyethyl(meth)acrylate, 2-hydroxypropyl (meth)acrylate, 3-hydroxypropyl (meth)acrylate, cyclopropyl(meth)acrylate, cyclopentyl(meth)acrylate, cyclohexyl (meth)acrylate, 4-methoxycyclohexyl(meth) acrylate, 2-cyclopentyloxycarbonylethyl (meth)acrylate, 2-cyclohexyloxycarbonylethyl(meth)acrylate, and 2-(4-methoxycyclohexyl)oxycarbonylethyl(meth)acrylate;

α-hydroxymethylacrylic acid esters; unsaturated nitryl compounds; unsaturated amide compounds; nitrogen-containing vinyl compounds; unsaturated carboxylic acids (anhydrides) such as a (meth)acrylic acid, a crotonic acid, a maleic acid, a maleic anhydride, a fumaric acid, an itaconic acid, an itaconic anhydride, a citraconic acid, a citraconic anhydride, and a mesaconic acid; carboxyl group-containing esters of unsaturated carboxylic acid having no bridged hydrocarbon skeleton such as 2-carboxyethyl(meth)acrylate, 2-carboxypropyl (meth)acrylate, 3-carboxypropyl(meth) acrylate, 4-carboxybutyl(meth)acrylate, and 4-carboxycyclohexyl(meth)acrylate; and (meth)acryloyloxylactone compounds having an acid-dissociable group; and (meth) acryloyloxylactone compounds having no acid-dissociable group;

as well as polyfunctional compounds such as polyfunctional compounds having a bridged hydrocarbon skeleton such as 1,2-adamantanediol di(meth)acrylate, 1,3-adamantanediol di(meth)acrylate, 1,4-adamantanediol di(meth)acrylate, and tricyclodecanyldimethylol di(meth)acrylate; and polyfunctional compounds such as polyfunctional compounds having no bridged hydrocarbon skeleton.

Among the above other compounds, (meth)acrylates having a bridged hydrocarbon skeleton are preferable.

It is preferable for the polymer of the embodiment of the present invention to include at least one compound from the group consisting of the compounds of the formula (1), (2), or (3), the compound shown by the formula (4), and the compound shown by the formula (6) as monomers.

The ratio of the monomers varies according to the combination of the monomers. The following ratios are indicated as mol % based on the total amount of all repeating units. The ratios are examples of when the polymer of the embodiment of the present invention is used in the radiation-sensitive resin.

(a) Combination of the compound shown by the formula (1), the compound shown by the formula (4), and the compound shown by the formula (6):

The amount of the compound shown by the formula (1) is 30 mol % or less, preferably from 1 to 30 mol %, and more preferably from 1 to 15 mol %. If less than 1 mol %, the sensitivity and developability tend to decrease, and if more than 30 mol %, transparency to radiation decreases, making it difficult to form a rectangular resist pattern.

The amount of the compound shown by the formula (4) is from 10 to 80 mol %, preferably from 15 to 75 mol %, and more preferably from 20 to 70 mol %. If less than 10 mol %, solubility of the radiation-sensitive resin composition in an alkaline developer tends to decrease, which may cause developing defects and impair developability. If more than 80%, solubility in the solvent forming the radiation-sensitive resin composition tends to decrease and resolution of the resist may be impaired.

(b) Combination of the compound shown by the formula (2) and/or the compound shown by the formula (3), the compound shown by the formula (4), and the compound shown by the formula (6):

The amount of the compound shown by the formula (2) and/or the compound shown by the formula (3) is from 1 to 20 mol %, and preferably from 1 to 10 mol %; the amount of the compound shown by the formula (4) is from 10 to 70 mol %, and preferably from 30 to 50 mol %; and the amount of the compound shown by the formula (6) is from 10 to 70 mol %, and preferably from 30 to 50 mol %.

If amount of the compound shown by the formula (2) and/or the compound shown by the formula (3) is more than 20 mol %, absorption of a radiation increases.

If amount of the compound shown by the formula (4) is less than 10 mol %, resolution decreases; if more than 70 mol %, etching tolerance is impaired.

If the amount of other compounds is less than 10 mol %, resolution decreases; if more than 70 mol %, solubility decreases.

Although the compound shown by the formula (2) and the compound shown by the formula (3) are preferably used individually, if they are used in combination, the molar ratio of the compound shown by the formula (2) to the compound shown by the formula (3) is from 1/0.1 to 1/100.

(c) Combination of the compound shown by the formula (2), in which A is —(CO)O-A'-, the compound shown by the formula (4), and the compound shown by the formula (6):

The amount of the compound shown by the formula (2) is from 0.1 to 100 mol %, and preferably from 0.1 to 20 mol %; the amount of the compound shown by the formula (4) is from 0 to 80 mol %, and preferably from 10 to 70 mol %; and the amount of the compound shown by the formula (6) is from 0 to 80 mol %, and preferably from 20 to 70 mol %.

In the case in which other compounds are added, the amount is 50 mol % or less, and preferably 30 mol % or less.

If amount of the compound shown by the formula (2) is more than 20 mol %, absorption increases and a trapezoidal pattern shape may be produced. If amount of the compound shown by the formula (4) is less than 10 mol %, resolution decreases; if more than 80 mol %, adhesion to substrates is impaired. If the amount of other compounds is more than 50 mol %, solubility decreases.

The polymer of the embodiment of the present invention is prepared by, for example, polymerizing the above compounds in an appropriate solvent in the presence of a chain transfer agent, as required, using a radical polymerization initiator such as hydroperoxides, dialkyl peroxides, diacyl peroxides, and azo compounds. As examples of the solvent used for polymerization, alkanes such as n-pentane, n-hexane, n-heptane, n-octane, n-nonane, and n-decane; cycloalkanes such as cyclohexane, cycloheptane, cyclooctane, decalin, and norbornane; aromatic hydrocarbons such as benzene, toluene, xylene, ethylbenzene, and cumene; halogenated hydrocarbons such as chlorobutanes, bromohexanes, dichloroethanes, hexamethylene dibromide, and chlorobenzene; saturated carboxylic acid esters such as ethyl acetate, n-butyl acetate, i-butyl acetate, and methyl propionate; ketones such as 2-butanone, 4-methyl-2-pentanone, and 2-heptanone; and ethers such as tetrahydrofuran, dimethoxyethanes, and diethoxyethanes can be given. These solvents may be used either individually or in combination of two or more. The polymerization temperature is usually from 40 to 120° C., and preferably from 50 to 90° C. The reaction time is usually from 1 to 48 hours, and preferably from 1 to 24 hours.

The weight average molecular weight (hereinafter referred to as "Mw") of the polymer determined by gel permeation chromatography is from 1,000 to 100,000, preferably from 1,500 to 80,000, and more preferably from 2,000 to 50,000. If the Mw of the polymer is less than 1,000, heat resistance as a resist may be decreased. If the Mw exceeds 100,000, developability as a resist may be decreased. The ratio of the Mw to the number average molecular weight (hereinafter called "Mn") (Mw/Mn) is usually from 1 to 5, and preferably from 1 to 3. It is preferable that the polymer contain almost no impurities such as halogens or metals. The smaller the amount of such impurities, the better are the sensitivity, resolution, process stability, pattern shape, or the like as a resist. The polymer can be purified using, for example, a chemical purification method such as washing with water or liquid-liquid extraction or a combination of the chemical purification method and a physical purification method such as ultra-filtration or centrifugation. In the embodiment of the present invention, the polymers can be used either individually or in combination of two or more.

In the embodiment of the present invention, in addition to monomers containing an acid generator on the side chain, other photoacid generators (hereinafter referred to as "other acid generators") can be used. As examples of the other acid generators, onium salts, sulfone compounds, and the like can be given. Examples of these other acid generators are given below.

(1) Onium Salt Compound

As examples of the onium salt, iodonium salt, sulfonium salt, phosphonium salt, diazonium salt, and pyridinium salt can be given. Specific examples of the onium salt include: diphenyliodoniumtrifluoromethanesulfonate, diphenyliodoniumnonafluoro-n-butanesulfonate, diphenyliodoniumperfluoro-n-octanesulfonate, bis(4-t-butylphenyl)iodoniumtrifluoromethanesulfonate, bis(4-t-butylphenyl)iodoniumnonafluoro-n-butanesulfonate, bis(4-t-butylphenyl)iodoniumperfluoro-n-octanesulfonate, cyclohexyl.2-oxocyclohexyl.methylsulfonium trifluoromethanesulfonate, dicyclohexyl.2-oxocyclohexylsulfonium trifluoromethanesulfonate, 2-oxocyclohexyldimethylsulfonium trifluoromethanesulfonate, bis(4-t-butylphenyl)iodoniumnonafluorobutanesulfonate, bis(4-t-butylphenyl)iodoniumtrifluoromethanesulfonate, bis(4-t-butylphenyl)iodoniumperfluorooctanesulfonate, bis(4-t-butylphenyl)iodonium-p-toluenesulfonate, bis(4-t-butylphenyl)iodonium-10-camphorsulfonate, 4-trifluoromethylbenzensulfonate, bis(4-t-butylphenyl)iodoniumperfluorobenzenesulfonate, diphenyliodonium-p-toluenesulfonate, diphenyliodoniumbenzenesulfonate, diphenyliodonium-10-camphorsulfonate, diphenyliodonium-4-trifluoromethylbenzenesulfonate, diphenyliodoniumperfluorobenzenesulfonate, bis(p-fluorophenyl)iodoniumtrifluoromethanesulfonate, bis(p-fluorophenyl)iodoniumnonafluoromethanesulfonate, bis(p-fluorophenyl)iodonium-10-camphorsulfonate, (p-fluorophenyl)(phenyl)iodoniumtrifluoromethanesulfonate, triphenylsulfoniumnonafluorobutanesulfonate, triphenylsulfoniumtrifluoromethanesulfonate, triphenylsulfoniumperfluorooctanesulfonate, triphenylsulfonium-2-bicyclo[2.2.1]hept-2-yl-1,1-difluoroethanesulfonate, triphenylsulfonium-2-bicyclo[2.2.1]hept-2-yl-1,1,2,2-tetrafluoroethanesulfonate, triphenylsulfonium-p-toluenesulfonate, triphenylsulfoniumbenzenesulfonate, triphenylsulfonium-10-camphorsulfonate, triphenylsulfonium-4-trifluoromethylbenzenesulfonate, triphenylsulfoniumperfluorobenzenesulfonate, 4-hydroxyphenyl.diphenylsulfonium trifluoromethanesulfonate, tris (p-methoxyphenyl)sulfonium nonafluorobutanesulfonate, tris(p-methoxyphenyl)sulfoniumtrifluoromethanesulfonate, tris(p-methoxyphenyl)sulfoniumperfluorooctanesulfonate, tris(p-methoxyphenyl)sulfonium-p-toluenesulfonate, tris(p-methoxyphenyl)sulfoniumbenzenesulfonate, tris(p-methoxyphenyl)sulfonium10-camphorsulfonate, tris(p-fluorophenyl)sulfoniumtrifluoromethanesulfonate, tris(p-fluorophenyl)sulfonium-p-toluenesulfonate, (p-fluorophenyl)diphenylsulfoniumtrifluoromethanesulfonate, 4-butoxy-1-naphthyltetrahydrothiophenium nonafluorobutanesulfonate, and 4-butoxy-1-naphthyltetrahydrothiophenium 2-bicyclo[2.2.1]hept-2-yl-1,1,2,2-tetrafluoroethanesulfonate.

(2) Sulfonic Acid Compound

As examples of the sulfonic acid compound, alkyl sulfonate, alkylimide sulfonate, haloalkyl sulfonate, aryl sulfonate, and imino sulfonate can be given. As specific examples of the sulfone compound, benzointosylate, tris(trifluoromethanesulfonate) of pyrogallol, nitrobenzyl-9,10-diethoxyanthracene-2-sulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimide trifluoromethanesulfonate, N-hydroxysuccinimide nonafluoro-n-butanesulfonate, N-hydroxysuccinimide perfluoro-n-octanesulfonate, 1,8-naphthalenedicarboxylic acid imide trifluoromethanesulfonate, 1,8-naphthalenedicarboxylic acid imide nonafluoro-n-butanesulfonate, and 1,8-naphthalenedicarboxylic acid imide perfluoro-n-octanesulfonate can be given.

Among these acid generators, diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl.2-oxocyclohexylmethylsulfonium trifluoromethanesulfonate, dicyclohexyl.2-oxocyclohexylsulfonium trifluoromethanesulfonate, 2-oxocyclohexyldimethylsulfonium trifluoromethanesulfonate, trifluoromethanesulfonylbicyclo[2.2.1]hept-5-ene-2,3-dicarbodiimide, nonafluoro-n-butanesulfonylbicyclo[2.2.1] hept-5-ene-2,3-dicarbodiimide, perfluoro-n-octanesulfonylbicyclo[2.2.1]hept-5-ene-2,3-dicarbodiimide, N-hydroxysuccinimide trifluoromethanesulfonate, N-hydroxysuccinimide nonafluoro-n-butanesulfonate, N-hydroxysuccinimide perfluoro-n-octanesulfonate, 1,8-naphthalenedicarboxylic acid imide trifluoromethanesulfonate, triphenylsulfoniumnonafluorobutanesulfonate, triphenylsulfoniumtrifluoromethanesulfonate, triphenylsulfonium-2-bicyclo[2.2.1]hept-2-yl-1,1-difluoroethanesulfonate, triphenylsulfonium-2-bicyclo[2.2.1]hept-2-yl-1,1,2,2-tetrafluoroethanesulfonate, 4-butoxy-1-naphthyltetrahydrothipheniumnonafluorobutanesulfonate, and 4-butoxy-1-naphthyltetrahydrothiophenium-2-bicyclo [2.2.1]hept-2-yl-1,1,2,2-tetrafluoroetha nesulfonate are preferable. These other acid generators may be used either individually or in combination of two or more.

The total amount of the recurring unit derived from the formulas (1), (2), and (3) and the other acid generators included in the copolymer of the embodiment of the present invention is usually from 0.5 to 30 parts by weight, and preferably from 1 to 25 parts by weight for 100 parts by weight of the resin from the viewpoint of ensuring sensitivity and developability as a resist. If this total amount is more than 30 parts by weight, a rectangular resist pattern may not be formed due to decreased radiation transmittance. The ratio of the other acid generators is usually 70 parts by weight or less, preferably from 0 to 50 parts by weight, and still more preferably from 0 to 30 parts by weight for 100 parts by weight of the recurring unit derived from the formula (1).

Various types of additives such as acid diffusion controllers, alicyclic additives having an acid-dissociating group, surfactants, and sensitizers may optionally be added to the radiation-sensitive resin composition of the embodiment of the present invention.

The acid diffusion controllers control diffusion of an acid generated from the acid generator upon exposure in the resist film to suppress undesired chemical reactions in the unexposed area. The addition of such an acid diffusion controller improves storage stability of the resulting radiation-sensitive resin composition and resolution as a resist. Moreover, the addition of the acid diffusion controller prevents the line width of the resist pattern from changing due to changes in the post-exposure delay (PED) between exposure and post exposure heat treatment, whereby a composition with remarkably superior process stability can be prepared. As the acid diffusion controller, nitrogen-containing organic compounds of which the basicity does not change due to exposure or heat treatment during formation of a resist pattern are preferable. As examples of such a nitrogen-containing organic compound, compounds shown by the following formula (7) (hereinafter called "nitrogen-containing compounds (a)"), compounds having two nitrogen atoms in the molecule (hereinafter called "nitrogen-containing compounds (b)"), polyamino compounds or polymers having three or more nitrogen atoms (hereinafter collectively called "nitrogen-containing compounds (c)"), amide group-containing compounds, and nitrogen-containing heterocyclic compounds can be given.

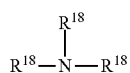

(7)

wherein $R^{18}$ independently represents a hydrogen atom, a substituted or unsubstituted, linear, branched, or cyclic alkyl group, a substituted or unsubstituted aryl group, or a substituted or unsubstituted aralkyl group.

Examples of the nitrogen-containing compounds (a) include mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; aromatic amines such as aniline, 2,6-diisopropylaniline, N-methylaniline, N,N-dimethylaniline, 2-methylaniline, 3-methylaniline, 4-methylaniline, 4-nitroaniline, diphenylamine, triphenylamine, and naphthylamine; and alicyclic amines such as N-t-butoxycarbonyl-4-hydroxypiperidine and 3-piperidino-1,2-propanediol.

Examples of the nitrogen-containing compound (b) include ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, and bis(2-diethylaminoethyl)ether. As examples of the nitrogen-containing compound (c), polyethyleneimine, polyallylamine, and a polymer of 2-dimethylaminoethylacrylamide can be given.

As examples of the amide group-containing compounds of the above-mentioned nitrogen group-containing compound (c), N-t-butoxycarbonyl group-containing amino compounds such as N-t-butoxycarbonyl di-n-octylamine, N-t-butoxycarbonyl di-n-nonylamine, N-t-butoxycarbonyl di-n-decylamine, N-t-butoxycarbonyl dicyclohexylamine, N-t-butoxycarbonyl-1-adamantylamine, N-t-butoxycarbonyl-N-methyl-1-adamantylamine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, and N-t-butoxycarbonyl-2-phenylbenzimidazole; formamide; N-methylformamide; N,N-dimethylformamide; acetamide; N-methylacetamide; N,N-dimethylacetamide; propioneamide; benzamide; pyrrolidone; N-methylpyrrolidone; and the like can be given.

Of these nitrogen-containing organic compounds, the nitrogen-containing compounds (a), amide group-containing compounds, nitrogen-containing heterocyclic compounds, and the like are preferable. The acid diffusion controller may be used either individually or in combination of two or more.

The alicyclic additives having an acid-dissociable group improve dry etching resistance, pattern shape, and adhesion to the substrate. As examples of the alicyclic additives, adamantane derivatives such as t-butyl 1-adamantanecarboxylate, t-butoxycarbonylmethyl 1-adamantanecarboxylate, di-t-butyl 1,3-adamantanedicarboxylate, t-butyl 1-adamantaneacetate, t-butoxycarbonylmethyl 1-adamantaneacetate, and di-t-butyl 1,3-adamantanediacetate; deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; and the like can be given. These alicyclic additives may be used either individually or in combination of two or more.

The surfactants improve applicability, striation, developability, and the like. As examples of the surfactant, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; and commercially available products such as KP341 (manufactured by Shin-Etsu Chemical Co., Ltd.), POLYFLOW No. 75 and No. 95 (manufactured by Kyoeisha Chemical Co., Ltd.), FTOP EF301, EF303, and EF352 (manufactured by Tohkem Products Corp.), MEGAFAC F171 and F173 (manufactured by Dainippon Ink and Chemicals, Inc.), Fluorad FC430 and FC431 (manufactured by Sumitomo 3M Ltd.), Asahi Guard AG710 and Surflon S-382, SC-101, SC-102, SC-103, SC-104, SC-105, and SC-106 (manufactured by Asahi Glass Co., Ltd.) can be given. The surfactants may be used either individually or in combination of two or more.

As other additives, low molecular weight alkali solubility controllers containing an alkali-soluble resin and/or acid dissociable protecting group, halation inhibitors, preservation stabilizers, antifoaming agents, and the like can be given.

The radiation-sensitive resin composition of the embodiment of the present invention is usually made into a composition solution by dissolving the composition in a solvent so that the total solid content is usually from 5 to 50 wt %, and preferably from 10 to 25 wt %, and filtering the solution using a filter with a pore diameter of about 200 nm, for example.

Examples of the solvents that can be used for preparing the composition solution include: linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; and alkyl 3-alkoxypropionates such as methyl 3-methoxypropionate, ethyl 3-methoxypropionate, methyl 3-ethoxypropionate, and ethyl 3-ethoxypropionate; as well as other solvents such as n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether, propylene glycol monoethyl ether, propylene glycol mono-n-propyl ether, toluene, xylene, ethyl 2-hydroxy-2-methyl propionate, ethyl ethoxyacetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutylbutyrate, ethyl acetate, n-propyl acetate, n-butyl acetate, methyl acetoacetate, ethyl acetoacetate, methyl pyruvate, ethyl pyruvate, N-methylpyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, and propylene carbonate.

These solvents may be used either individually or in combination of two or more. Among these solvents, linear or branched ketones, cyclic ketones, propylene glycol monoalkyl ether acetates, alkyl 2-hydroxypropionates, and alkyl 3-alkoxypropionates are preferable.

The radiation-sensitive resin composition of the embodiment of the present invention is particularly useful as a chemically-amplified resist. In the embodiment of the present invention, an acid-dissociable group in the resin dissociates by an action of an acid which is generated from an acid generating component in the resin and an acid generator upon exposure, thereby producing carboxyl groups. As a result, solublity of the exposed part of the resist in an alkaline developer increases, whereby the exposed part is dissolved in an alkaline developer and removed to form a positive-tone resist pattern.

A resist pattern is formed from the radiation-sensitive resin composition of the embodiment of the present invention by applying the composition solution to, for example, substrates such as a silicon wafer or a wafer coated with aluminum using an appropriate application method such as rotational coating, cast coating, and roll coating to form a resist film. The resist film is then optionally pre-baked (hereinafter called "PB") and exposed to form a predetermined resist pattern. As radiation used for exposure, visible rays, ultraviolet rays, deep ultraviolet rays, X-rays, electron beams, or the like are appropriately selected. It is particularly preferable to use deep ultraviolet rays represented by an ArF excimer laser (wavelength: 193 nm) and a KrF excimer laser (wavelength: 248 nm). The ArF excimer laser (wavelength: 193 nm) is particularly preferable. In the embodiment of the present invention, it is preferable to perform post-exposure bake (hereinafter called "PEB"). PEB ensures smooth dissociation of the acid-dissociable group in the resin (A). The heating temperature for the PEB is usually 30 to 200° C., and preferably 50 to 170° C., although the heating conditions are changed depending on the composition of the radiation-sensitive resin composition.

In order to bring out the maximum potentiality of the radiation-sensitive resin composition of the embodiment of the present invention, an organic or inorganic anti-reflection film may be formed on a substrate as disclosed in JP-B-6-12452, for example. Moreover, a protection film may be formed on the resist film as disclosed in JP-A-5-188598, for example, in order to prevent the effects of basic impurities and the like in an environmental atmosphere. These techniques may be employed in combination. The exposed resist film is then developed to form a prescribed resist pattern. As preferable examples of the developer used for development, alkaline aqueous solutions prepared by dissolving at least one of alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, and 1,5-diazabicyclo-[4.3.0]-5-nonene are given. The concentration of the alkaline aqueous solution is usually 10 wt % or less. If the concentration of the alkaline aqueous solution exceeds 10 wt %, an unexposed area may also be dissolved in the developer.

Organic solvents or the like may be added to the developer containing the alkaline aqueous solution. As examples of the organic solvent, ketones such as acetone, methyl ethyl ketone, methyl i-butyl ketone, cyclopentanone, cyclohexanone, 3-methylcyclopentanone, and 2,6-dimethylcyclohexanone; alcohols such as methylalcohol, ethylalcohol, n-propylalcohol, i-propylalcohol, n-butylalcohol, t-butylalcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol; acetonylacetone; and dimethylformamide can be given. These organic solvents may be used either individually or in combination of two or more. The amount of the organic solvent to be used is preferably 100 vol % or less of the alkaline aqueous solution. The amount of the organic solvent exceeding 100 vol % may decrease developability, giving rise to a larger undeveloped portion in the exposed area. In addition, surfactants or the like may be added to the developer containing the alkaline aqueous solution in an appropriate amount. After development using the alkaline aqueous solution developer, the resist film is generally washed with water and dried.

EXAMPLES

The present invention is described below in more detail by examples. However, these examples should not be construed as limiting the present invention. In the examples, "part" refers to "part by weight" unless otherwise indicated.

Measurement and evaluation in Examples and Comparative Examples were carried out according to the following procedures.

Mw:

The weight average molecular weight of polymers (A-1), (A-2), (A-21), (A-22), and (R-3) were measured on a polystyrene-reduced basis, using GPC columns (manufactured by Tosoh Corp., G2000H$^{XL}$x2, G3000H$^{XL}$x1, G4000H$^{XL}$x1) under the following conditions. flow rate: 1.0 ml/minute, eluate: tetrahydrofuran, column temperature: 40° C., standard reference material: monodispersed polystyrene The polymers (A-3) to (A-20), (R-1), and (R-2) were detected using a MALLS detector, and Mw was measured by gel permeation chromatography (GPC) using a GPC column (TSK gel α-2500 and TSK gel α-M manufactured by Tosoh Corp.) under the following analysis conditions. flow rate: 1.0 ml/minute, eluate: dimethylformamide with 30 mmol/l LiBr and 10 mmol/l H$_3$PO$_4$ dissolved therein, column temperature: 40° C., detector: MALLS (DAWN DSP manufactured by Wyatt Co., cell type K5, laser wavelength: 632.8 nm)

Sensitivity:

(1) Examples 15 to 18 and Comparative Example 2

The composition was applied to a wafer substrate, on which an ARC 25 film with a thickness of 82 nm (manufactured by Brewer Science) had been formed, by spin coating and baked on a hot plate at 100° C. for 60 seconds (Example 15, Example 16, and Comparative Example 2) or at 130° C. for 60 seconds (Example 17 and Example 18) to form a resist coating with a thickness of 200 nm. The coating was exposed to light through a mask pattern using an ArF excimer laser photolithographic machine manufactured by Nikon Corp. (lens numerical aperture: 0.85, exposure wavelength: 193 nm). After performing PEB at 110° C. for 60 seconds (Example 15, Example 16, and Comparative Example 2) or at 130° C. for 60 seconds (Example 17 and Example 18), the resist film was developed at 23° C. for 60 seconds in a 2.38 wt % TMAH aqueous solution by the paddle method, washed with water, and dried to form a positive-tone resist pattern. An optimum dose at which a 1:1 line-and-space pattern with a line width of 100 nm was formed through a 1:1 line-and-space mask with a size of 100 nm was taken as "sensitivity". In Examples 42 to 50 and Comparative Example 5, PB and PEB were carried out at 110° C. for 60 seconds.

(2) Other Examples

In the Examples and Comparative Examples, the composition was applied to a wafer substrate, on which an ARC 29A film with a thickness of 77 nm (manufactured by Nissan Chemical Industries, Ltd.) had been formed, by spin coating and baked on a hot plate at 100° C. for 90 seconds to form a resist coating with a thickness of 200 nm. The coating was exposed to light through a mask pattern using a full field reduced projection exposure apparatus (S306C, manufactured by Nikon Corp., lens numerical aperture: 0.75). After performing PEB at 110° C. for 90 seconds, the resist film was developed at 25° C. for 60 seconds in a 2.38 wt % TMAH aqueous solution, washed with water, and dried to form a positive-tone resist pattern. An optimum dose at which a 1:1 line-and-space pattern with a line width of 100 nm was formed through a 1:1 line-and-space mask with a size of 100 nm was taken as "sensitivity".

Resolution:

Minimum dimensions of the resist pattern resolved at the optimum dose were taken as the resolution.

Pattern shape:

The dimensions of the lower side La and the upper side Lb of the rectangular cross-section of a line and space pattern (1L1S) with a line width of 100 nm formed on a silicon wafer were measured using a scanning electron microscope. The pattern shapes are shown in FIG. 1. The pattern shape was judged as "Good" when $0.85 \leq Lb/La \leq 1$ was satisfied, and otherwise evaluated as "Bad".

LER:

In the observation of a 100 nm 1L/1S pattern developed with an optimum dose of exposure, the line width was inspected from above the pattern using SEM (scanning electron microscope) S9220 manufactured by Hitachi, Ltd. to measure the difference between the line width at the point at which the irregularity produced along the horizontal side of the line patterns is most conspicuous and the designed line width of 100 nm.

The line width was inspected at arbitrary points from above the pattern and the fluctuation of the measurement was evaluated by 3 Sigma.

DOF:

A 100 nm line-and-space pattern (1L1S) was exposed at an optimal dose of radiation under the conditions in which the depth of focus was offset at an interval of 0.05 μm in a range from −1.0 μm to +1.0 μm. The range (μm) in which the line width was from 90 nm (−10%) to 110 nm (+10%) was taken as DOF.

The evaluation as a composition for the liquid immersion lithographic method was carried out according to the following (1) to (4).

(1) Amount of elusion (amount of elusion of acid generator and acid diffusion controller)

A 30 cm×30 cm square silicone rubber sheet with a thickness of 1.0 mm (manufactured by Kureha Elastomer Co., Ltd.), from the center of which a disk with a diameter of 11.3 cm was cut out, was superposed on the center of an 8-inch silicon wafer (hereinafter referred to as "wafer (1)") which was previously treated with HMDS (hexamethyldisilazane) at 100° C. for 60 seconds using "CLEAN TRACK ACT8" (manufactured by Tokyo Electron, Ltd.). The circular area of the center of the silicone rubber sheet, from which a disk was removed, was filled with 10 ml of ultra pure water using a 10 ml whole pipette.

Next, an underlayer antireflection film with a thicknesses of 77 nm ("ARC29A" manufactured by Bruwer Science) was formed on the silicon rubber sheet above using CLEAN TRACK ACT8, and an 8-inch silicon wafer (hereinafter referred to as "wafer (2)") on which a resist film with a thicknesses of 205 nm was formed by applying resist compositions shown in Tables 3 and 6 on the underlayer antireflection film by spin coating using the CLEAN TRACK ACT8 and baking at 115° C. for 60 seconds, was superposed in a manner such that the resist coating surface came come in contact with the silicon rubber and the ultra pure water did not leak from the silicon rubber.

The superposed material of the two sheets of wafers was turned out and maintained for 10 seconds with the wafer (2) being the bottom, and then turned out again to make the wafer (2) to face up. Ultra pure water was collected from the wafer (1) using a glass injector to be used as a sample for analysis. The recovery rate of the ultra-pure water after completion of the experiment was 95% or more.

The amount of the recurring unit or the anion part of the acid generator originating in the formula (01) in the collected ultra pure water was measured using LC-MS (a liquid chromatograph mass spectrometer, LC section: "SERIES 1100" manufactured by AGILENT Corp., MS section: "Mariner" manufactured by Perseptive Biosystems, Inc.) under the following conditions. In this case, aqueous solutions of triphenylsulfonium nonafluoro-n-butanesulfonate with a concentration of 1 ppb, 10 ppb, and 100 ppb were prepared, and each peak intensity originating from the anion part was measured in the same manner as above under the following conditions to prepare a calibration curve. The amount of elusion was calculated from the above-mentioned peak intensity using the calibration curve.

(Measurement Conditions)

Column: One column of "CAPCELL PAK MG" manufactured by Shiseido Co., Ltd.

Flow rate: 0.2 ml/min

Solvent: A 3:7 mixture of water and methanol, with 0.1 wt % of formic acid

Measurement temperature: 35° C.

(2) Sensitivity of Liquid Immersion Lithography

A 12-inch silicon wafer on which an underlayer antireflection film with a thickness of 77 nm ("ARC29A" manufactured by Bruwer Science) had been formed was used as a substrate. "CLEAN TRACK ACT12" (manufactured by Tokyo Electron Ltd.) was used for preparing the underlayer antireflection film.

Resist coatings with a thickness of 150 nm were formed on the above-mentioned substrate by spin coating the resin compositions shown in Table 3 and Table 6 using Clean Track Act 12 and baking at 100° C. for 90 seconds. The resist coatings were exposed to radiation through a mask pattern using an ArF excimer laser exposure apparatus ("TWIN SCAN XT1250i" manufactured by ASML, lighting conditions: NA 0.85 sigma 0.93/0.69). After PEB at 110° C. for 90 seconds, the resist coatings were developed at 23° C. for 30 seconds in a 2.38 wt % tetramethylammonium hydroxide aqueous solution, washed with water, and dried to form positive-tone resist patterns. An optimum dose at which a 1:1 line-and-space (1L1S) pattern with a line width of 90 nm was formed was taken as sensitivity, using a scanning electron microscope ("S-9380" manufactured by Hitachi High-Technologies Corporation).

(3) Resolution of Liquid Immersion Lithography

The minimum line and space dimension resolved by an optimum dose of irradiation was taken as the resolution. A scanning electron microscope ("S-9380" manufactured by Hitachi High-Technologies Corporation) was used for the measurement.

(4) Pattern Shape Formed by Liquid Immersion Lithography

The cross-sectional configuration of a 90 nm line-and-space pattern was inspected using "S-9380" manufactured by Hitachi High-Technologies Corporation to measure the line width Lb in the middle and the line width La on the upper part of the coating. The configurations were judged as "Good" when $0.9 \leq (La-Lb)/Lb \leq 1.1$ was satisfied, and otherwise as "Bad".

Example 1

A compound shown by the formula (1-1) was synthesized by the following method.

100 g of vinyl sulfonic acid and 50 g of triphenylsulfonium bromide were dissolved in water and the solution was stirred at room temperature for one hour. After evaporating water under reduced pressure, the residue was extracted with 300 g of methanol. The methanol was evaporated from the resulting methanol solution under reduced pressure to produce 51 g of triphenylsulfonium vinyl sulfonic acid (1-1). The compound was analyzed by $^1$H-NMR spectrum (JNM-EX270, manufactured by JEOL Ltd.) using deuterated chloroform as a solvent to show that the chemical shift was as follows, confirming that the compound was the target compound.

$^1$H-NMR σ ppm (CD$_3$Cl): 6.25 (1H, d), 6.51 (1H, d), 6.88 (1H, dd), 7.26-7.78 (15H, m, Ph)

In addition, the compound was analyzed using a mass spectrometer ("JMS-AX505W" manufactured by JEOL Ltd.). A parent ion peak of 263 was detected to confirm that the compound was the target compound.

The mass spectrometry analysis of the compound (1-1) was carried out under the following conditions.

Apparatus: JMS-AX505W mass spectrometer (manufactured by JEOL Ltd.)

Emitter current: 5 mA (gas used: Xe)

Acceleration voltage: 3.0 kV

ION MULTI: 1.3

Ionization method: fast atom bombardment (FAB)

Detection ion: cation (+)

Measured mass range: 20-1,500 m/z

Scan: 30 sec

Resolution: 1,500

Matrix: 3-nitrobenzyl alcohol

Example 2

A compound shown by the formula (2-3) was synthesized by the following method.

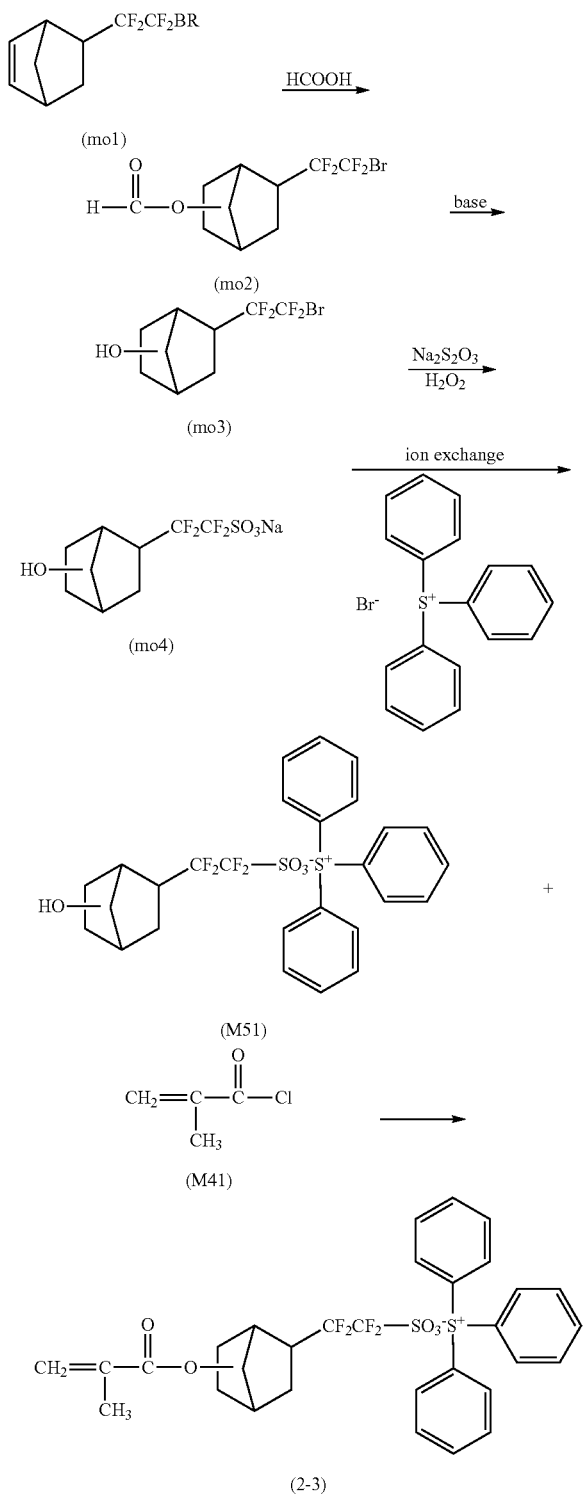

200 g of a compound (m01) was added to 331 g of formic acid and the mixture was stirred for 8 hours while refluxing under a nitrogen atmosphere. After the reaction, the reaction mixed solution was cooled to room temperature. Unreacted formic acid was evaporated under reduced pressure and 500 ml of ethyl acetate was added. The ethyl acetate solution was washed three times with 300 ml of a 5% aqueous solution of sodium hydrogencarbonate and washed three times with 300 ml of water. The ethyl acetate solution was dried using anhydrous magnesium sulfate. Ethyl acetate was evaporated under reduced pressure to produce a compound (m02) (amount: 230 g, yield: 98%). The compound (m02) was used in the next step as is.

230 g of the compound (m02) was dissolved in 1,500 ml of methanol. After adding 153 g of potassium carbonates, the mixture was stirred at a room temperature for two hours. After the reaction, insoluble salts were removed by filtration and methanol was evaporated under reduced pressure. The residue was dissolved in 1,500 ml of ethyl acetate and washed with water (500 ml×4). The organic layer was dried over anhydrous magnesium sulfate, filtered, and ethyl acetate was evaporated under reduced pressure. The resulting residue was distilled under reduced pressure (0.1 mmHg, 100° C.) to produce a compound (m03). (amount: 188 g, yield: 90%)

A 2 liter three-necked flask, in which the atmosphere was completely replaced with nitrogen, was charged with a solution of 11.8 g of sodium dithionite and 9.1 g of sodium hydrogencarbonate dissolved in 75 ml of water. 75 ml of a solution of 10 g of the compound (m03) dissolved in acetonitrile was added and the mixture was reacted for five hours at 80° C. After cooling, an acetonitrile layer was removed from the reaction solution parted into two layers. Acetonitrile was evaporated under reduced pressure from the separated acetonitrile layer. 56 g of water and 42 mg of sodium tungstate dehydrate were added to the residue and 3.5 g of 30% oxygenated water was added dropwise. The resulting mixture was stirred at 60° C. for one hour. The water was evaporated under reduced pressure to produce 13.6 g of a compound (m04).

13.6 g of the compound (m04) dissolved in methylene chloride was added to a solution of 17.5 g of triphenylsulfonium bromide dissolved in 75 ml of water. After stirring at room temperature for one hour, the organic layer was removed and washed twice with 50 ml of water, and the solvent was removed by evaporation under reduced pressure to prepare the target compound (M51) as a colorless viscous oil. The recovered amount was 12.7 g and the yield from the compound (m03) was 67%.

2 g of the compound (M51) was dissolved in 10 ml of methylene chloride and 1.1 g of triethylamine was added. After the addition, 0.5 g of methacrylic acid chloride (M41) was added dropwise. The mixture was heated to room temperature and stirred for three hours. After the reaction, the reaction mixture was washed five times with 30 ml of water. Methylene chloride was evaporated under reduced pressure to prepare a target compound (2-3). The amount of the product was 1.2 g and the yield was 52%.

NMR spectrum: $^1$H NMR 1.15-2.13 (11H, m), 3.72 (1H, m), 4.66 (1H, m), 5.53 (1H, m), 6.25 (1H, m), 7.8 (15H, m); mass spectrum: cation: 263 m/z and anion: 359 m/z

Example 3

An intermediate compound shown by the following formula (M52) was synthesized by the following method.

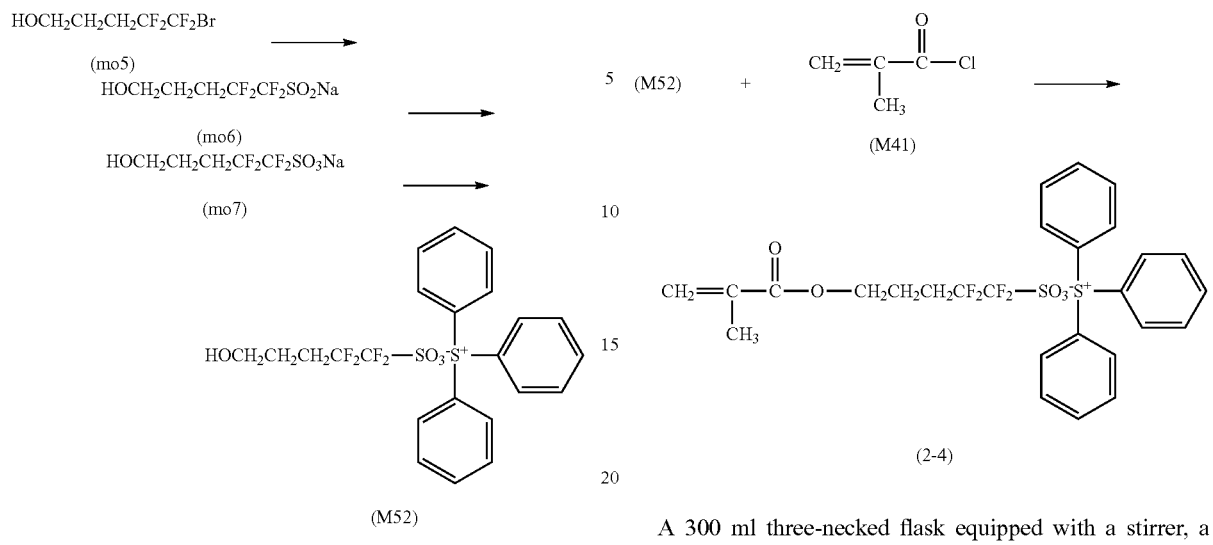

(M52)

A 300 ml four-necked flask equipped with a stirrer, a thermometer, a dropping funnel, and a reflux condenser was charged with 100 g of water, 14 g (0.080 mol) of sodium dithionate, and 10 g (0.12 mol) of sodium hydrogencarbonate. Next, a solution of 9.56 g (0.040 mol) of 5-bromo-4,4,5,5-tetrafluoropentan-1-ol (m05) dissolved in 80 g of acetonitrile was added from the dropping funnel over 15 minutes. After heating over an oil bath, the mixture was reacted at an internal temperature of 60° C. for five hours. After the reaction, the mixture was cooled to 25° C. and allowed to stand for 15 minutes to separate the reaction mixture into two layers. The organic layer was removed using a separating funnel. 100 g of acetonitrile was added to the water layer. The resulting organic layer was collected and combined with the previously removed organic layer. The whole organic layer was concentrated using a rotary evaporator. 80 ml of water was added to the residue, and 60 mg of sodium tungstate dihydrate was further added, followed by stirring for a while. After the addition of 4.5 g of 30 wt % oxygenated water, the mixture was heated at 60° C. for one hour. After the reaction, the reaction mixture was cooled to 25° C. and concentrated using an evaporator. 70 g of water and 100 g of chloroform were added to the concentrate, and the resulting mixture was stirred for a short time. Then, 14 g of triphenylsulfonium bromide was added, followed by stiffing for one hour. The organic layer was removed using a separating funnel. 100 g of chloroform was added to the water layer. The resulting organic layer was collected and combined with the previously removed organic layer. The collected organic layer was washed three times using 150 g of water and concentrated using an evaporator. The residual oil was purified using column chromatography to prepare 1,1,2,2-tetrafluoro-5-hydroxypentane-1-sulfonic acid triphenylsulfonium (M52). The amount of the product was 10.2 g and the yield was 71 wt %.

Mass spectrum: cation: 263 m/z, anion: 307 m/z

Elemental analysis: C, 54.79 wt %, H, 4.58%, S: 12.79 wt %

Example 4

A compound shown by the formula (2-4) was synthesized by the following method.

(M52) + (M41)

(2-4)

A 300 ml three-necked flask equipped with a stirrer, a thermometer, and a dropping funnel was charged with 15 g of 1,1,2,2-tetrafluoro-5-hydroxypentane-1-sulfonic acid triphenylsulfonium (Compound (M52), 0.03 mol) and 50 ml of methylene chloride. The mixture was cooled to −20° C. and stirred. After the addition of 4.55 g (0.045 mol) of triethylamine and stirring for a while, 5 g (0.048 mol) of methacrylic acid chloride (M41) was added dropwise over 15 minutes. The mixture was then heated to 25° C. and stirred for six hours. After the reaction, the reaction mixture was charged to 100 g of water and the organic layer was extracted using a separating funnel. 100 g of methylene chloride was added to the water layer. The resulting organic layer was collected and combined with the previously removed organic layer. The collected organic layer was washed three times using 150 g of water, and concentrated using an evaporator. The resulting oily product was purified by column chromatography to prepare the target compound (2-4). The amount of the product was 10.6 g and the yield was 63%.

NMR spectrum: $^1$H NMR [σ ppm (CD$_3$Cl): 1.91 (m, 3H), 1.99 (m, 2H), 2.46 (m, 2H), 4.15 (m, 2H), 5.53 (1H, m), 6.09 (1H, m), 7.67-7.83 (m, 15H)]

Mass spectrum: cation: 263 m/z, anion: 307 m/z

Example 5

A compound shown by the formula (2-5) was synthesized by the following method.

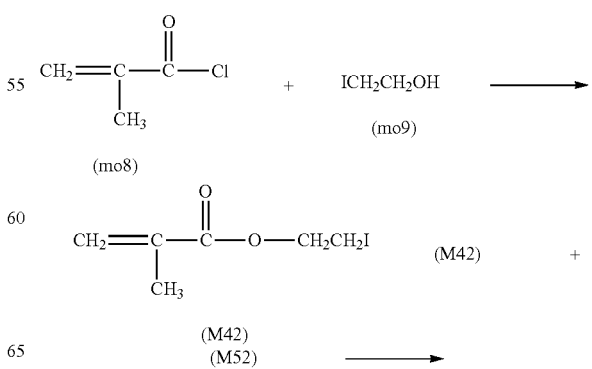

(M42)
(M52)

-continued

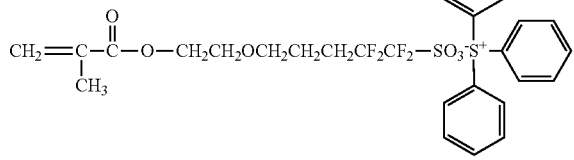

(2-5)

Under nitrogen atmosphere, a three-necked flask equipped with a stirrer and a dropping funnel was charged with 20.9 g (0.2 mol) of the compound (m08), which was dissolved in 160 ml of methylene chloride. The methylene chloride solution was cooled to 0° C. and 30.4 g (0.3 mol) of triethylamine was added, followed by further stirring. After adding dropwise 37.8 g (0.22 mol) of ethanol diiodide (m09) over 30 minutes, the reaction solution was heated to room temperature and stirred for two hours. After the reaction, the reaction solution was added to 300 ml of saturated ammonia chloride water and the methylene chloride layer was extracted using a separating funnel. The remaining water layer was extracted twice with 200 ml of methylene chloride. After removing the solvent from the collected methylene chloride layer, the residue was separated using column chromatography to prepare a compound (M42).

A 300 ml three-necked flask equipped with a stirrer, a thermometer, and a dropping funnel was charged with 15 g of 1,1,2,2-tetrafluoro-5-hydroxypentane-1-sulfonic acid triphenylsulfonium (Compound (M52), 0.03 mol) and 50 ml of methylene chloride. The mixture was cooled to −20° C. and stirred. After the addition of 4.55 g (0.045 mol) of triethylamine and stirring for a short time, 11.5 g (0.048 mol) of the compound (M42) was added dropwise over 15 minutes. The mixture was then heated to 25° C. and stirred for six hours. After the reaction, the reaction mixture was charged to 100 g of water and the organic layer was extracted using a separating funnel. 100 g of methylene chloride was added to the water layer. The resulting organic layer was collected and combined with the previously removed organic layer. The collected organic layer was washed three times using 150 g of water, and concentrated using an evaporator. The resulting oily product was purified by column chromatography to prepare the target compound (2-5). The amount of the product was 11.4 g and the yield was 62%.

NMR spectrum: $^1$H NMR [σ ppm (CD$_3$Cl): 1.92 (m, 3H), 1.99 (m, 2H), 2.42 (m, 2H), 3.64 (m, 2H), 4.34 (m, 2H), 4.55 (m, 2H), 5.56 (1H, dt), 6.13 (1H, dt), 7.63-7.78 (m, 15H)]

Mass spectrum: cation: 263 m/z, anion: 351 m/z

Example 6

A compound shown by the formula (3-2) was synthesized by the following method.

A 2 liter three-necked flask, in which the atmosphere was completely replaced with nitrogen, was charged with a solution of 70 g of sodium dithionite and 52 g of sodium hydrogencarbonate dissolved in 300 ml of water. 300 ml of a solution of 55 g of the compound (e1) dissolved in acetonitrile was added dropwise for one hour at room temperature and the mixture was reacted for two hours at 75° C. After evaporating the acetonitrile under reduced pressure, the reaction solution was extracted with ethyl acetate. The organic layer was washed with saturated brine and dried over anhydrous magnesium sulfate. The dried organic layer was distilled under reduced pressure to remove ethyl acetate to prepare 35 g of a compound (e2).

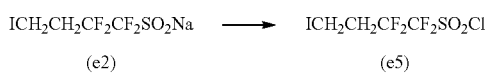

Next, a 2 liter eggplant flask was charged with a solution of 80 g of the compound (e2) dissolved in 250 ml of water. Superfluous chlorine gas was bubbled into the solution for more than 15 minutes while stirring at room temperature. The oily matter collected on the bottom of the flask was extracted with methylene chloride. The organic layer was washed with a sodium hydrogencarbonate aqueous solution and dried over anhydrous magnesium sulfate. The dried organic layer was distilled under reduced pressure to remove methylene chloride to prepare 68 g of a compound (e5).

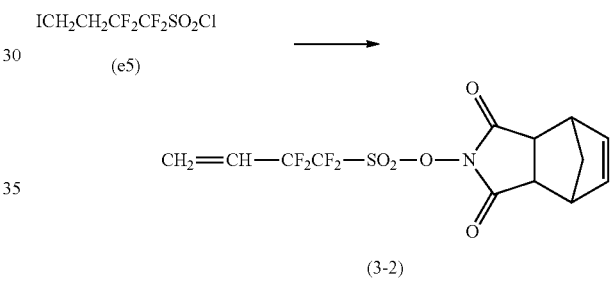

(3-2)

Next, after adding 22 g of N-hydroxy-5-norbornene-2,3-dicarboxylmide to a solution of 30 g of the compound (e5) dissolved in 150 g of tetrahydrofuran, 29 g of triethylamine was added to the mixture dropwise. After stiffing the reaction solution for 10 minutes at room temperature, water was added dropwise to prepare the reaction product as white crystals. After filtering, the crystals were dissolved in methylene chloride and the solution was consecutively washed with sodium hydrogencarbonate aqueous solution, oxalic acid aqueous solution, and water. After drying the solution over anhydrous magnesium sulfate, the methylene chloride was evaporated under reduced pressure to prepare 35 g of a compound (3-2).

The compound was analyzed by $^1$H-NMR spectrum (JNM-EX270, manufactured by JEOL Ltd.) using deuterated chloroform as a solvent to show that the chemical shift was as follows, confirming that the compound was the target compound.

$^1$HNMR [σ ppm (CD$_3$Cl): 1.53 (1H, d), 1.76-1.81 (1H, m), 3.12 (2H, s), 3.48 (2H, s), 6.17 (2H, s), 6.53 (1H, d), 6.88 (1H, d), 7.55 (1H, d)]

In addition, the compound was analyzed using a mass spectrometer ("JMS-AX505W" manufactured by JEOL Ltd.). A parent ion peak of 369 was detected to confirm that the compound was the target compound.

The mass spectrometry analysis of the compound (3-2) was carried out under the following conditions.

Apparatus: JMS-AX505W mass spectrometer (manufactured by JEOL Ltd.)

Emitter current: 5 mA (gas used: Xe)

Acceleration voltage: 3.0 kV

ION MULTI: 1.3

Ionization method: fast atom bombardment (FAB)

Detection ion: cation (+)

Measured mass range: 20-1,500 m/z

Scan: 30 sec

Resolution: 1,500

Matrix: 3-nitrobenzyl alcohol

Monomers other than the above-mentioned compounds used for the polymerization of the polymers (A-1) to (A-22) of the embodiment of the present invention and the other polymers (R-1) to (R-3) are shown as (M-1) to (M-8) below.

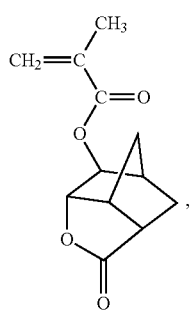

(M-1)

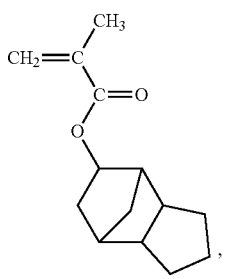

(M-2)

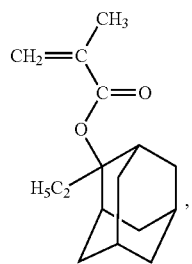

(M-3)

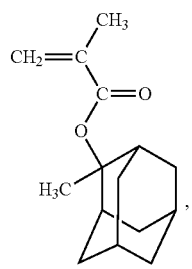

(M-4)

-continued

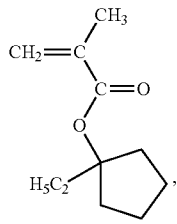

(M-5)

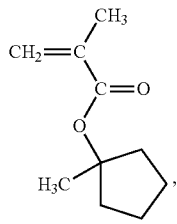

(M-6)

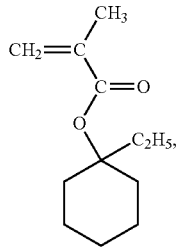

(M-7)

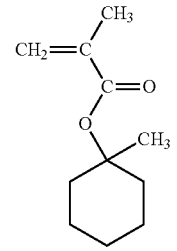

(M-8)

Example 7

-continued

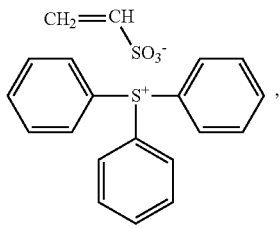
(1-1)

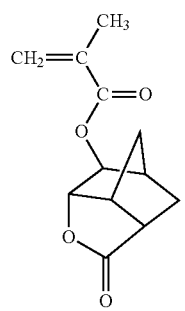
(M-1)

A monomer solution was prepared by dissolving 19.37 g (40 mol %) of compound (M-4), 7.66 g (10 mol %) of compound (1-1), and 22.97 g (50 mol %) of compound (M-1) in 300 g of 2-butanone, and further adding 3.40 g of dimethyl 2,2'-azobis(2-methylpropionate). A 1,000 ml three-necked flask charged with 100 g of 2-butanone was purged with nitrogen gas for 30 minutes. After the nitrogen purge, the flask was heated to 80° C. while stiffing and the above monomer solution was added dropwise using a dropping funnel over three hours. The polymerization reaction was carried out for six hours after initiation of the addition. After completion of polymerization, the polymer solution was cooled with water to 30° C. or lower and poured into 2,000 g of methanol. A white precipitate produced was collected by filtration.

The white powder collected by filtration was washed twice with 400 g of methanol in a slurry state, filtered again, and dried at 50° C. for 17 hours to prepare a polymer in the form of a white resin powder (72 g, yield 72%). The polymer was a copolymer with an Mw of 8,500, and the mol % ratio of the recurring units of the compound (M-4), compound (1-1), and compound (M-1) determined by $^{13}$C-NMR analysis was 39.9:11.1:49.0 (mol %). This copolymer is referred to as a polymer (A-1).

Example 8

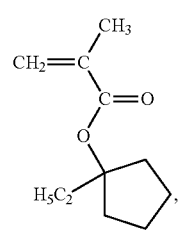
(M-5)

A monomer solution was prepared by dissolving 33.00 g (40 mol %) of compound (M-5), 16.71 g (10 mol %) of compound (1-1), and 50.29 g (50 mol %) of compound (M-1) in 300 g of 2-butanone, and further adding 3.72 g of dimethyl 2,2'-azobis(2-methylpropionate). A 1,000 ml three-necked flask charged with 100 g of 2-butanone was purged with nitrogen gas for 30 minutes. After the nitrogen purge, the flask was heated to 80° C. while stiffing, and the above monomer solution was added dropwise using a dropping funnel over three hours. The polymerization reaction was carried out for six hours after initiation of the addition. After completion of polymerization, the polymer solution was cooled with water to 30° C. or lower and poured into 2,000 g of methanol. A white precipitate produced was collected by filtration.

The white powder collected by filtration was washed twice with 400 g of methanol in a slurry state, filtered again, and dried at 50° C. for 17 hours to prepare a polymer in the form of a white resin powder (75 g, yield 75%). The polymer was a copolymer with an Mw of 7,800, and the mol % ratio of the recurring units of the compound (M-5), compound (1-1), and compound (M-1) determined by $^{13}$C-NMR analysis was 40.2:9.5:50.3 (mol %). This copolymer is referred to as a polymer (A-2).

Example 9

A monomer solution was prepared by dissolving 7.4 g (50 mol %) of compound (M-1), 5.5 g (45 mol %) of compound (M-5), and 2.1 g (5 mol %) of compound (2-3) in 45 g of 2-butanone, and further adding 0.27 g of AIBN. A 100 ml three-necked flask was charged with 15 g of 2-butanone and nitrogen gas was bubbled into the flask for 30 minutes. After the nitrogen purge, the flask was heated to 80° C. while stiffing, and the above monomer solution was added dropwise using a dropping funnel over three hours. The polymerization reaction was carried out for six hours after initiation of the addition. After completion of polymerization, the polymer solution was cooled with water to 30° C. or lower and poured into 100 g of 2-propanol. A white precipitate produced was collected by filtration.

The white powder collected by filtration was washed twice with 400 g of 2-propanol in a slurry state, filtered again, and

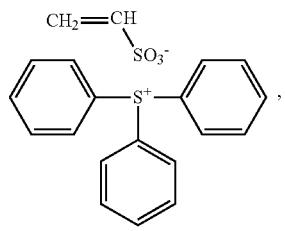
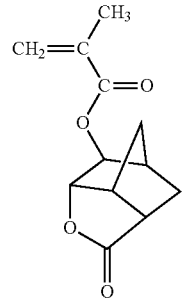

dried at 50° C. for 17 hours to prepare a polymer in the form of a white resin powder (10 g, yield 68%). The polymer was a copolymer with an Mw of 30,000 and an Mw/Mn of 1.44 (result of MALLS). The mol % ratio of the recurring units of the compound (M-1), the compound (M-5), and the compound (2-3) determined by $^{13}$C-NMR analysis was 55:41:4 (mol %). This copolymer is referred to as a polymer (A-3).

Example 10

The polymers (A-4) to (A-12) of the embodiment of the present invention and the other polymers (R-1) and (R-2) were prepared in the same manner as in Example 9. Mw and Mw/Mn (result of MALLS) of each polymer were as follows.

Polymer (A-4): (M-1)/(M-4)/(M-5)/(2-3)=48/34/15/3, Mw=18,000, Mw/Mn=2.2

Polymer (A-5): (M-1)/(M-2)/(M-5)/(2-3)=48/10/39/3, Mw=16,000, Mw/Mn=2.1

Polymer (A-6): (M-1)/(M-6)/(2-3)=48/49/3, Mw=13,000, Mw/Mn=1.9

Polymer (A-7): (M-1)/(M-3)/(M-7)/(2-3)=48/34/15/3, Mw=18,000, Mw/Mn=2.5

Polymer (A-8): (M-1)/(M-4)/(M-8)/(2-3)=48/34/15/3, Mw=24,000, Mw/Mn=2.8

Polymer (A-9): (M-1)/(M-4)/(M-5)/(2-4)=48/34/15/3, Mw=14,000, Mw/Mn=1.8

Polymer (A-10): (M-1)/(M-5)/(2-4)=48/49/3, Mw=14,000, Mw/Mn=1.9

Polymer (A-11): (M-1)/(M-4)/(M-5)/(2-3)=48/33/14/5, Mw=17,000, Mw/Mn=1.9

Polymer (A-12): (M-1)/(M-5)/(2-3)=46/48/6, Mw=17,000, Mw/Mn=2.1

Polymer (R-1): (M-1)/(M-4)/(M-5)=50/36/14, Mw=14,000, Mw/Mn=2.0

Polymer (R-2): (M-1)/(M-5)=51.2/48.8, Mw=12,000, Mw/Mn=1.9

Example 11

A monomer solution was prepared by dissolving 7.5 g (50 mol %) of the compound (M-1), 5.5 g (45 mol %) of the compound (M-5), and 2.0 g (5 mol %) of the compound (2-5) in 45 g of 2-butanone, and further adding 0.27 g of AIBN. A 100 ml three-necked flask was charged with 15 g of 2-butanone, and nitrogen gas was bubbled into the flask for 30 minutes. After the nitrogen purge, the flask was heated to 80° C. while stirring, and the above monomer solution was added dropwise using a dropping funnel over three hours. The polymerization reaction was carried out for six hours after initiation of the addition. After completion of polymerization, the polymer solution was cooled with water to 30° C. or lower and poured into 100 g of 2-propanol. A white precipitate produced was collected by filtration.

The white powder collected by filtration was washed twice with 400 g of 2-propanol in a slurry state, filtered again, and dried at 50° C. for 17 hours to prepare a polymer in the form of a white resin powder (10 g, yield 68%). The polymer was a copolymer with an Mw of 28,000 and an Mw/Mn of 1.8 (result of MALLS). The mol % ratio of the recurring units of the compound (M-1), the compound (M-5), and the compound (2-5) determined by $^{13}$C-NMR analysis was 54:41:5 (mol %). This copolymer is referred to as a polymer (A-13).

Example 12

The polymers (A-13) to (A-19) of the embodiment of the present invention were prepared in the same manner as in Example 11. Mw and Mw/Mn (result of MALLS) of each polymer were as follows.

Polymer (A-14): (M-1)/(M-4)/(M-5)/(2-5)=48/34/15/3, Mw=25,000, Mw/Mn=1.8

Polymer (A-15): (M-1)/(M-5)/(2-5)=48/49/3, Mw=14,000, Mw/Mn=1.6

Polymer (A-16): (M-1)/(M-2)/(M-5)/(2-5)=48/10/39/3, Mw=15,000, Mw/Mn=1.5

Polymer (A-17): (M-1)/(M-3)/(M-5)/(2-5)=48/34/15/3, Mw=22,000, Mw/Mn=1.7

Polymer (A-18): (M-1)/(M-4)/(M-6)/(2-5)=48/34/15/3, Mw=19,000, Mw/Mn=1.6

Polymer (A-19): (M-1)/(M-4)/(M-7)/(2-5)=48/34/15/3, Mw=25,000, Mw/Mn=1.8

Polymer (A-20): (M-1)/(M-4)/(M-8)/(2-5)=48/34/15/3, Mw=22,000, Mw/Mn=1.7

Example 13

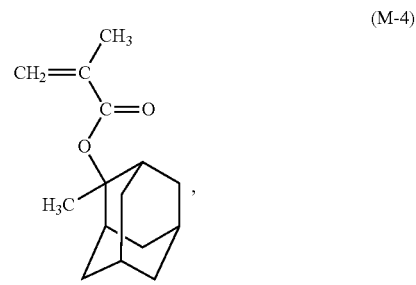

(M-4)

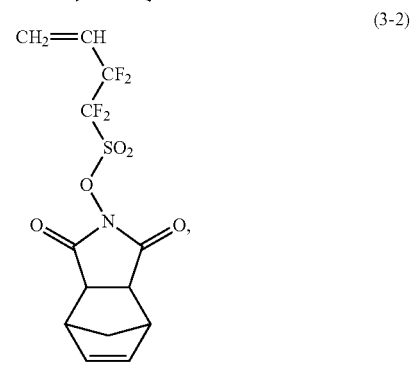

(3-2)

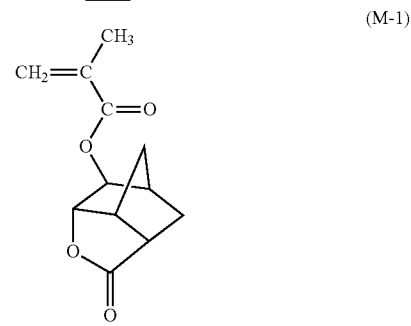

(M-1)

A monomer solution was prepared by dissolving 15.27 g (10 mol %) of the compound (3-2), 38.77 g (40 mol %) of the compound (M-4), and 45.96 g (50 mol %) of the compound (M-1) in 300 g of 2-butanone, and further adding 3.40 g of dimethyl 2,2'-azobis(2-methylpropionate). A 1,000 ml three-necked flask was charged with 100 g of 2-butanone and nitrogen gas was bubbled into the flask for 30 minutes. After the nitrogen purge, the flask was heated to 80° C. while stiffing, and the above monomer solution was added dropwise using a dropping funnel over three hours. The polymerization reaction was carried out for six hours after initiation of the addition. After completion of polymerization, the polymer solution was cooled with water to 30° C. or lower and poured into 2,000 g of methanol. A white precipitate produced was collected by filtration.

The white powder collected by filtration was washed twice with 400 g of methanol in a slurry state, filtered again, and dried at 50° C. for 17 hours to prepare a polymer in the form of a white resin powder (72 g, yield 72%). The polymer was a copolymer with an Mw of 8,500 and the mol % ratio of the recurring units of the compound (3-2), the compound (M-4), and the compound (M-1) determined by $^{13}$C-NMR analysis was 11.1:39.9:49.0 (mol %). This copolymer is referred to as a polymer (A-21).

Example 14 compound (M-5), and 50.29 g (50 mol %) of the compound (M-1) in 300 g of 2-butanone, and further adding 3.72 g of dimethyl 2,2'-azobis(2-methylpropionate). A 1,000 ml three-necked flask was charged with 100 g of 2-butanone, and nitrogen gas was bubbled into the flask for 30 minutes. After the nitrogen purge, the flask was heated to 80° C. while stiffing, and the above monomer solution was added dropwise using a dropping funnel over three hours. The polymerization reaction was carried out for six hours after initiation of the addition. After completion of polymerization, the polymer solution was cooled with water to 30° C. or lower and poured into 2,000 g of methanol. A white precipitate produced was collected by filtration.

The white powder collected by filtration was washed twice with 400 g of methanol in a slurry state, filtered again, and dried at 50° C. for 17 hours to prepare a polymer in the form of a white resin powder (75 g, yield 75%). The polymer was a copolymer with an Mw of 7800 and the mol % ratio of the recurring units of the compound (3-2), the compound (M-5), and the compound (M-1) determined by $^{13}$C-NMR analysis was 9.5:40.2:50.3 (mol %). This copolymer is referred to as a polymer (A-22).

Comparative Example 1

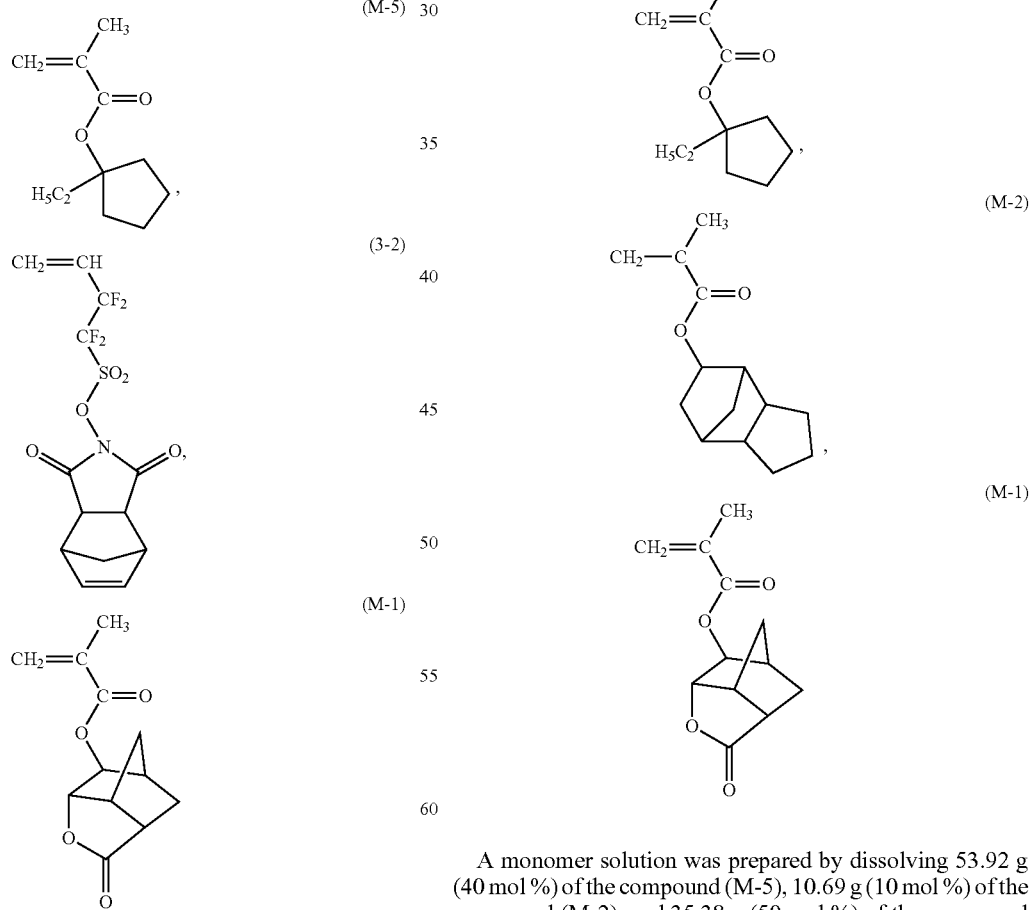

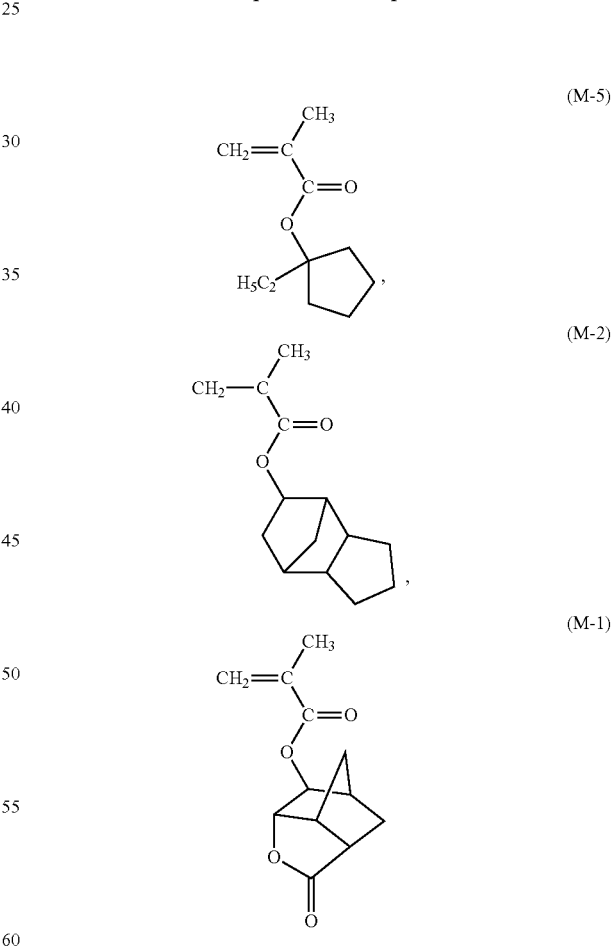

A monomer solution was prepared by dissolving 16.71 g (10 mol %) of the compound (3-2), 33.00 g (40 mol %) of the A monomer solution was prepared by dissolving 53.92 g (40 mol %) of the compound (M-5), 10.69 g (10 mol %) of the compound (M-2), and 35.38 g (50 mol %) of the compound (M-1) in 300 g of 2-butanone, and further adding 2.24 g of dimethyl 2,2'-azobis(2-methylpropionate). A 1,000 ml three-necked flask was charged with 100 g of 2-butanone, and nitrogen gas was bubbled into the flask for 30 minutes. After the nitrogen purge, the flask was heated to 80° C. while stiffing, and the above monomer solution was added dropwise using a dropping funnel over three hours. The polymerization reaction was carried out for six hours after initiation of the addition. After completion of polymerization, the polymer solution was cooled with water to 30° C. or lower and poured into 2,000 g of methanol. A white precipitate produced was collected by filtration.

The white powder collected by filtration was washed twice with 400 g of methanol in a slurry state, filtered again, and dried at 50° C. for 17 hours to prepare a polymer in the form of a white resin powder (72 g, yield 72%). The polymer was a copolymer with an Mw of 8,500 and the mol % ratio of the recurring units of the compound (M-5), the compound (M-2), and the compound (M-1) determined by $^{13}$C-NMR analysis was 39.8:8.0:52.2 (mol %). This copolymer is referred to as a polymer (R-3).

Examples 15 to 50 and Comparative Examples 2 to 5

Components shown in Tables 1, 3, 6, and 9 (wherein part(s) indicates part(s) by weight) were mixed to prepare homogeneous solutions. The solutions were filtered through a membrane filter with a pore diameter of 200 nm to prepare the solution compositions of Examples and Comparative Examples. The following components were used in Examples and Comparative Examples. The radiation-sensitive resin compositions prepared were evaluated according to the above-mentioned methods.

The results of Examples 15 to 18 and Comparative Example 2 are shown in Table 2, and the results of Examples 19 to 31 and Comparative Example 3 are shown in Tables 4 and 5, the results of Examples 32 to 41 and Comparative Example 4 are shown in Tables 7 and 8, and the results of Examples 42 to 50 and Comparative Example 5 are shown in Table 10.

(1) Acid generator (B)

B-1: triphenylsulfonium trifluoromethanesulfonate

B-2: 4-n-butoxy-1-naphthyltetrahydrothiophenium nonafluorobutanesulfonate

B-3: Triphenylsulfonium nonafluoro-n-butanesulfonate (2) Acid diffusion controller (D)

D-1: N-t-butoxycarbonyl-4-hydroxypiperidine

D-2: 3-pyperidino(piperidino)-1,2-propanediol

D-3: 2,6-diisopropylaniline (3) Solvent (C)

C-1: propylene glycol monomethyl ether acetate

C-2: 2-heptanone

D-3: cyclohexanone

D-4: γ-butyrolactone (4) Additive (D)

D-1: Following formula (AD-1)

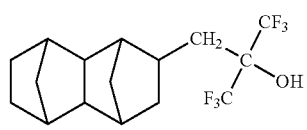

TABLE 1

| | Resin (part) | Acid generator (B) (part) | Acid diffusion controller (D) (part) | Additive (part) | Solvent (C) (part) |
|---|---|---|---|---|---|
| Example | | | | | |
| 15 | A-1(100) | B-1(1) B-2(6) | D-2(0.50) | AD-1(2) | C-1(700) C-3(300) C-4(10) |
| 16 | A-2(100) | B-1(1) B-2(6) | D-2(0.50) | AD-1(2) | C-1(700) C-3(300) C-4(10) |
| 17 | A-1(100) | — | — | AD-1(2) | C-1(700) C-3(300) C-4(10) |
| 18 | A-2(100) | — | — | AD-1(2) | C-1(700) C-3(300) C-4(10) |
| Comparative example | | | | | |
| 2 | R-3(100) | 8-1(5) | D-2(0.50) | AD-1(2) | C-1(700) C-3(300) C-4(10) |

TABLE 2

| | Sensitivity (J/m$^2$) | Resolution (nm) | Pattern shape | LER (nm) |
|---|---|---|---|---|
| Example | | | | |
| 15 | 200 | 90 | Good | 4.9 |
| 16 | 190 | 90 | Good | 4.8 |
| 17 | 220 | 85 | Good | 5.5 |
| 18 | 230 | 85 | Good | 5.8 |
| Comparative example | | | | |
| 2 | 210 | 100 | Bad | 7.8 |

TABLE 3

| | Resin (part) | Acid generator (B) (part) | Acid diffusion controller (D) (part) | Solvent (C) (part) |
|---|---|---|---|---|
| Example | | | | |
| 19 | A-1(100) | — | D-3(0.20) | C-1(650) C-2(200) |
| 20 | A-2(100) | — | D-2(0.20) | C-1(650) C-2(200) |
| 21 | A-3(100) | — | D-3(0.20) | C-1(650) C-2(200) |
| 22 | A-4(100) | — | D-1(0.20) | C-1(650) C-2(200) |
| 23 | A-5(100) | — | D-2(0.20) | C-1(650) C-3(200) |

TABLE 3-continued

| | Resin (part) | Acid generator (B) (part) | Acid diffusion controller (D) (part) | Solvent (C) (part) |
|---|---|---|---|---|
| 24 | A-6(100) | — | D-2(0.20) | C-1(650) C-3(200) |
| 25 | A-1(50) R-1(50) | — | D-2(0.20) | C-1(650) C-3(200) |
| 26 | A-1(50) R-2(50) | B-1(1) | D-3(0.20) | C-1(650) C-3(200) |
| 27 | A-1(100) | B-1(1) | D-2(0.30) | C-1(650) C-3(200) |
| 28 | A-7(100) | — | D-3(0.20) | C-1(650) C-2(200) |
| 29 | A-8(100) | — | D-1(0.20) | C-1(650) C-2(200) |
| 30 | A-9(100) | — | D-2(0.20) | C-1(650) C-3(200) |
| 31 | A-10(100) | — | D-2(0.20) | C-1(650) C-3(200) |
| Comparative example | | | | |
| 3 | R-2(100) | B-1(4) | D-2(0.50) | C-1(450) C-3(200) |

TABLE 4

| | Sensitivity ($J/m^2$) | Resolution (nm) | DOF (μm) | LER |
|---|---|---|---|---|
| Example | | | | |
| 19 | 460 | 90 | 0.6 | 4.9 |
| 20 | 470 | 90 | 0.6 | 4.8 |
| 21 | 540 | 90 | 0.7 | 5.0 |
| 22 | 440 | 90 | 0.6 | 5.2 |
| 23 | 560 | 90 | 0.7 | 5.3 |
| 24 | 540 | 90 | 0.7 | 4.9 |
| 25 | 580 | 90 | 0.6 | 5.2 |
| 26 | 460 | 90 | 0.7 | 5.3 |
| 27 | 660 | 90 | 0.6 | 5.2 |
| 28 | 540 | 90 | 0.6 | 4.9 |
| 29 | 550 | 90 | 0.6 | 4.7 |
| 30 | 560 | 90 | 0.7 | 4.9 |
| 31 | 540 | 90 | 0.6 | 4.9 |
| Comparative example | | | | |
| 3 | 580 | 100 | 0.5 | 7.6 |

TABLE 5

| | Sensitivity of liquid immersion lithography ($J/m^2$) | Resolution of liquid immersion lithography (nm) | Amount of acid generator elusion (ppb) | Pattern shape formed by liquid immersion lithography |
|---|---|---|---|---|
| Example | | | | |
| 19 | 340 | 85 | Undetected | 1.0 (Good) |
| 20 | 450 | 85 | Undetected | 1.0 (Good) |
| 21 | 350 | 85 | Undetected | 1.0 (Good) |
| 22 | 320 | 85 | Undetected | 0.9 (Good) |
| 23 | 440 | 85 | Undetected | 1.1 (Good) |
| 24 | 350 | 85 | Undetected | 1.0 (Good) |
| 25 | 360 | 85 | Undetected | 1.0 (Good) |
| 26 | 350 | 85 | Undetected | 1.1 (Good) |
| 27 | 370 | 85 | Undetected | 0.9 (Good) |
| 28 | 360 | 85 | Undetected | 1.0 (Good) |
| 29 | 360 | 85 | Undetected | 1.1 (Good) |
| 30 | 380 | 85 | Undetected | 0.9 (Good) |
| 31 | 360 | 85 | Undetected | 1.0 (Good) |
| Comparative example | | | | |
| 3 | 420 | 95 | 441 | 1.2 (Bad) |

TABLE 6

| | Resin (part) | Acid generator (B) (part) | Acid diffusion controller (D) (part) | Solvent (C) (part) |
|---|---|---|---|---|
| Example | | | | |
| 32 | A-13(100) | — | D-3(0.30) | C-1(650) C-2(200) |
| 33 | A-14(100) | — | D-2(0.20) | C-1(650) C-2(200) |
| 34 | A-15(100) | — | D-3(0.20) | C-1(650) C-2(200) |
| 35 | A-16(100) | — | D-1(0.20) | C-1(650) C-2(200) |
| 36 | A-17(100) | — | D-2(0.20) | C-1(650) C-3(200) |
| 37 | A-18(100) | — | D-2(0.20) | C-1(650) C-3(200) |
| 38 | A-19(100) | — | D-2(0.20) | C-1(650) C-3(200) |
| 39 | A-20(100) | — | D-2(0.20) | C-1(650) C-3(200) |
| 40 | A-14(50) R-1(50) | — | D-2(0.20) | C-1(650) C-3(200) |
| 41 | A-14(50) R-1(50) | B-1(1) | D-2(0.20) | C-1(650) C-2(200) |
| Comparative example | | | | |
| 4 | R-2(100) | B-1(4) | D-2(0.50) | C-1(450) C-3(200) |

TABLE 7

| | Sensitivity ($J/m^2$) | Resolution (nm) | DOF (μm) | LER |
|---|---|---|---|---|
| Example | | | | |
| 32 | 190 | 90 | 0.7 | 3.9 |
| 33 | 180 | 90 | 0.6 | 3.8 |
| 34 | 190 | 90 | 0.7 | 3.8 |
| 35 | 180 | 90 | 0.6 | 3.9 |
| 36 | 180 | 90 | 0.6 | 3.7 |
| 37 | 190 | 90 | 0.7 | 3.9 |
| 38 | 190 | 90 | 0.7 | 3.8 |
| 39 | 190 | 90 | 0.7 | 3.9 |
| 40 | 170 | 90 | 0.6 | 3.8 |
| 41 | 150 | 90 | 0.7 | 3.9 |
| Comparative example | | | | |
| 4 | 280 | 100 | 0.5 | 7.4 |

TABLE 8

|  | Sensitivity of liquid immersion lithography (J/m²) | Resolution of liquid immersion lithography (nm) | Amount of acid generator elusion (ppb) | Pattern shape formed by liquid immersion lithography |
|---|---|---|---|---|
| Example |  |  |  |  |
| 32 | 120 | 85 | Undetected | 0.9 (Good) |
| 33 | 130 | 85 | Undetected | 1.0 (Good) |
| 34 | 120 | 85 | Undetected | 1.0 (Good) |
| 35 | 120 | 85 | Undetected | 0.9 (Good) |
| 36 | 130 | 85 | Undetected | 1.1 (Good) |
| 37 | 120 | 85 | Undetected | 1.0 (Good) |
| 38 | 130 | 85 | Undetected | 1.0 (Good) |
| 39 | 130 | 85 | Undetected | 1.1 (Good) |
| 40 | 140 | 85 | Undetected | 0.9 (Good) |
| 41 | 110 | 85 | 90 | 1.0 (Good) |
| Comparative example |  |  |  |  |
| 4 | 190 | 95 | 425 | 1.2 (Bad) |

TABLE 9

|  | Resin (part) | Acid generator (B) (part) | Acid diffusion controller (D) (part) | Additive (part) | Solvent (C) (part) |
|---|---|---|---|---|---|
| Example |  |  |  |  |  |
| 42 | A-21(100) | B-1(5) | D-1(0.3) | AD-1(2) | C-1(700) C-3(300) C-4(10) |
| 43 | A-22(100) | B-1(5) | D-2(0.3) | AD-1(2) | C-1(700) C-3(300) C-4(10) |
| 44 | A-21(100) | B-1(1) B-2(6) | D-2(0.5) | AD-1(2) | C-1(700) C-3(300) C-4(10) |
| 45 | A-22(100) | B-1(1) B-2(6) | D-2(0.5) | AD-1(2) | C-1(700) C-3(300) C-4(10) |
| 46 | A-21(100) | B-1(2) | D-1(0.3) | AD-1(2) | C-1(700) C-3(300) C-4(10) |
| 47 | A-22(100) | B-1(2) | D-1(0.3) | AD-1(2) | C-1(700) C-3(300) C-4(10) |
| 48 | A-21(100) | — | — | AD-1(2) | C-1(700) C-3(300) C-4(10) |
| 49 | A-22(100) | — | — | AD-1(2) | C-1(700) C-3(300) C-4(10) |
| 50 | A-21(50) A-22(50) | B-1(1) B-2(6) | D-2(0.5) | AD-1(2) | C-1(700) C-3(300) C-4(10) |
| Comparative example |  |  |  |  |  |
| 5 | R-3(100) | B-1(5) | D-1(0.3) | AD-1(2) | C-1(700) C-3(300) C-4(10) |

TABLE 10

|  | Sensitivity (J/m²) | Resolution (nm) | Pattern shape | LER (nm) |
|---|---|---|---|---|
| Example |  |  |  |  |
| 42 | 250 | 85 | Good | 4.9 |
| 43 | 270 | 85 | Good | 4.8 |
| 44 | 220 | 85 | Good | 4.6 |
| 45 | 230 | 80 | Good | 5.2 |
| 46 | 280 | 85 | Good | 4.9 |
| 47 | 290 | 85 | Good | 5.1 |
| 48 | 250 | 80 | Good | 4.2 |
| 49 | 280 | 80 | Good | 4.5 |
| 50 | 210 | 85 | Good | 5.1 |
| Comparative example |  |  |  |  |
| 5 | 200 | 100 | Bad | 7.8 |

As clear from Tables 5 and 8, no peak originating from the anion part of the amount of acid generator elusion was found in the radiation-sensitive resin composition of the embodiment of the present invention.

As a polymer which can be used as the resin component of the radiation-sensitive resin composition, a polymer having an —SO$_3^-$ group on a side chain can be prepared by polymerizing monomers containing the compound shown by the formula (1) or formula (2). In the case of the compound of the formula (2), in particular, a polymer having an —SO$_3^-$ group on a side chain, in which a perfluoroalkyl group and the like are bonded to the carbon atom on the α-position of a sulfonyl group, can be prepared. A polymer having an —SO$_2$— group on a side chain can be prepared by polymerizing monomers containing the compound shown by the formula (3). These polymers are homogeneously dispersed in the polymer chain and produce an acid by irradiation. In addition, the structure in which the acid is suspended from the polymer chain provides only a short average dispersion length for the acid and substantially limits the range of dispersion. These characteristics enable the polymer containing an acid generator of the embodiment of the present invention to control diffusion of the acid after exposure in the liquid immersion lithography, ensure high resolution, and improve LER.

The radiation-sensitive resin composition, in which a resin containing the acid generator of the embodiment of the present invention is used, is useful as a chemically-amplified resist responsive to deep ultraviolet rays represented by a KrF excimer laser (wavelength: 248 nm) and an ArF excimer laser (wavelength: 193 nm). Since the resist is highly sensitive and particularly has a wide DOF and excellent LER, the resin composition is suitably used for fabrication of integrated circuit devices that are expected to be more and more miniaturized in the future.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A compound represented by the following formula (5),

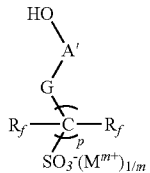
(5)

wherein at least one of $R_f$ groups represents a fluorine atom or a linear or branched perfluoroalkyl group having 1 to 10 carbon atoms, A' represents a substituted or unsubstituted, linear or branched alkylene group having 1 to 20 carbon atoms, an alkylene group having at least one hetero atom, or a single bond, G represents a divalent organic group having a fluorine atom or a single bond, $M^{m+}$ represents an onium cation, m represents a natural number of 1 to 3, and p represents a natural number of 1 to 8.

* * * * *